United States Patent
Stoessel et al.

(10) Patent No.: US 9,181,289 B2
(45) Date of Patent: Nov. 10, 2015

(54) METAL COMPLEXES

(75) Inventors: Philipp Stoessel, Frankfurt am Main (DE); Esther Breuning, Ober-Ramstadt (DE); Dominik Joosten, Frankfurt am Main (DE)

(73) Assignee: Merck Patent GmbH (DE)

( * ) Notice: Subject to any disclaimer, the term of this patent is extended or adjusted under 35 U.S.C. 154(b) by 835 days.

(21) Appl. No.: 13/501,351

(22) PCT Filed: Sep. 24, 2010

(86) PCT No.: PCT/EP2010/005857
§ 371 (c)(1),
(2), (4) Date: Apr. 11, 2012

(87) PCT Pub. No.: WO2011/044988
PCT Pub. Date: Apr. 21, 2011

(65) Prior Publication Data
US 2012/0199794 A1     Aug. 9, 2012

(30) Foreign Application Priority Data
Oct. 16, 2009   (DE) .................. 10 2009 049 587

(51) Int. Cl.
| C09K 11/06 | (2006.01) |
| C07F 15/00 | (2006.01) |
| H01L 51/00 | (2006.01) |
| C09B 57/00 | (2006.01) |
| C09B 57/10 | (2006.01) |
| H01L 51/50 | (2006.01) |

(52) U.S. Cl.
CPC .......... *C07F 15/0033* (2013.01); *C07F 15/0086* (2013.01); *C09B 57/00* (2013.01); *C09B 57/10* (2013.01); *H01L 51/0085* (2013.01); *H01L 51/5016* (2013.01); *Y02E 10/549* (2013.01)

(58) Field of Classification Search
CPC ...... C09B 57/00; C09B 57/10; Y02E 10/549; H01L 51/5016; H01L 51/0085; C07F 15/0033; C07F 15/0086
USPC ............... 252/301.16; 544/225; 546/4
See application file for complete search history.

(56) References Cited

U.S. PATENT DOCUMENTS

| 2008/0214818 A1 | 9/2008 | Chin et al. |
| 2011/0284799 A1 | 11/2011 | Stoessel et al. |

FOREIGN PATENT DOCUMENTS

| DE | 102009007038 A1 | 8/2010 |
| JP | 2001-081453 A | 3/2001 |
| JP | 5245117 B2 * | 7/2013 |
| TW | 201041886 A | 12/2010 |
| WO | WO-2007088768 A1 | 8/2007 |

OTHER PUBLICATIONS

Machine translation of JP 5245117.*
Brooks et al., "Synthesis and Characterization of Phosphorescent Cyclometalated Platinum Complexes," Inorg. Chem., 2002, 41, p. 3055-3066.*
International Search Report for PCT/EP2010/005857 mailed Dec. 9, 2010.
Koning et al., "Specific and Selective Reduction of Aromatic Nitrogen Heterocycles with the BIS-Pyridine Complexes of BIS(1,4-Dihydro-1-Pyridyl)Zinc and BIS(1,4-Dihydro-1-Pyridyl)Magnesium", Journal of Organometallic Chemistry, vol. 199, No. 2, p. 153-169 (1980).
Besten et al., "Intramolecular Electron-Transfer Induced Carbon-Hydrogen Bond Dissociation in Methyl-Substituted 1,10-Phenanthroline Complexes of Bis($\eta^5$-cyclopentadienyl)titanium", Journal of the American Chemical Society, vol. 102, No. 18, p. 5969-5971 (1980).
Schröder et al., "Radical-Like Activation of Alkanes by the Ligated Copper Oxide Cation (Phenanthroline)CuO++", Journal of Physical Chemistry B, vol. 108, No. 38, pp. 14407-14416 (2004).
Zhang et al., "Designed Assembly and Structures and Photoluminescence of a New Class of Discrete ZnII Complexes of 1*H*-1,10-Phenanthroline-2-one", European Journal of Inorganic Chemistry, No. 17, p. 3407-3412 (2006).
English Translation of Japanese Office Action mailed on Sep. 30, 2014 for Application No. 2012-533505.
English Translation of Taiwan Search Report for Application No. 099134895 dated Aug. 8, 2014.

* cited by examiner

*Primary Examiner* — Ling Choi
*Assistant Examiner* — Catherine S Branch
(74) *Attorney, Agent, or Firm* — Drinker Biddle & Reath LLP

(57) ABSTRACT

The present invention relates to metal complexes and to electronic devices, in particular organic electroluminescent devices, comprising these metal complexes.

18 Claims, No Drawings

METAL COMPLEXES

CROSS-REFERENCE TO RELATED APPLICATIONS

This application is a national stage application (under 35 U.S.C. §371) of PCT/EP2010/005857, filed Sep. 24, 2010, which claims benefit of German application 10 2009 049 587.8, filed Oct. 16, 2009.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement in OLEDs which exhibit triplet emission, in particular with respect to efficiency, operating voltage and lifetime.

In accordance with the prior art, the triplet emitters employed in phosphorescent OLEDs are, in particular, iridium and platinum complexes. An improvement in these OLEDs has been achieved by employing metal complexes containing polypodal ligands or cryptates, as a consequence of which the complexes have higher thermal stability, which results in a longer lifetime of the OLEDs (WO 04/081017, WO 05/113563, WO 06/008069). Here too, however, further improvements are still desirable.

The prior art furthermore discloses iridium complexes which contain imidazophenanthridine derivatives or diimidazoquinazoline derivatives as ligands (WO 07/095,118). Here too, further improvements with respect to efficiency, operating voltage and lifetime are still desirable.

The object of the present invention is therefore to provide novel metal complexes which are suitable as emitters for use in OLEDs.

Surprisingly, it has been found that certain metal chelate complexes described in greater detail below achieve this object and exhibit good properties in the organic electroluminescent device, in particular with respect to the operating voltage, the efficiency and the emission colour. The present invention therefore relates to these metal complexes and to organic electroluminescent devices which comprise these complexes.

The invention thus relates to a compound of the formula (1)

formula (1)

where the compound of the general formula (1) contains a moiety $M(L)_n$ of the formula (2):

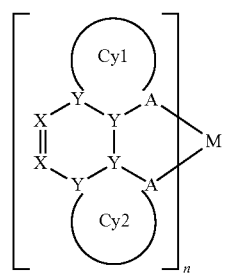
formula (2)

where the following applies to the symbols and indices used:

M is a metal;

Y is on each occurrence, identically or differently, C or N; a double bond may in each case also be present between the two atoms Y or between the adjacent atoms Y and A which are bonded in Cy1, or between the two atoms Y or the adjacent atoms Y and A which are bonded in Cy2;

Cy1 is on each occurrence, identically or differently, a six-membered ring or a five-membered ring together with the group A and the two groups Y, where one group Y in Cy1 stands for C and the other group Y in Cy1 stands for N if Cy1 represents a six-membered ring and where both groups Y in Cy1 stand for C or both stand for N if Cy1 represents a five-membered ring; Cy1 here may be substituted by one or more radicals R;

if Cy1 stands for a six-membered ring, a five-membered or six-membered aryl or heteroaryl ring group, which may be substituted by one or more radicals R, may also be condensed onto Cy1;

characterised in that Cy1 contains at least one group Z as part of the ring;

Z is selected, identically or differently on each occurrence, from the group consisting of C(=O), C(=S), $CR_2$, NR, O, S, PR or P(=O)R, where at least one group Z is equal to C(=O), C(=S), $CR_2$ or P(=O)R if Cy1 represents a five-membered ring;

Cy2 is on each occurrence, identically or differently, Cy1 or is on each occurrence, identically or differently, an aryl or heteroaryl group together with the group A and the two groups Y, where both groups Y in Cy2 stand for C if Cy2 stands for a six-membered aryl or heteroaryl ring group; Cy2 here may be substituted by one or more radicals R;

A is on each occurrence, identically or differently, C or N;

X is on each occurrence, identically or differently, CR or N;

R is on each occurrence, identically or differently, H, D, F, Cl, Br, I, $N(R^1)_2$, $P(R^1)_2$, CN, $NO_2$, $Si(R^1)_3$, $B(OR^1)_2$, C(=O)$R^1$, P(=O)$(R^1)_2$, S(=O)$R^1$, S(=O)$_2R^1$, $OSO_2R^1$, OH, SH, $O^-$, $S^-$, $N(R^1)^-$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^1$, where one or more non-adjacent $CH_2$ groups may be replaced by $R^1C=CR^1$, C≡C, $Si(R^1)_2$, $Ge(R^1)_2$, $Sn(R^1)_2$, C=O, C=S, C=Se, C=NR$^1$, P(=O)($R^1$), SO, $SO_2$, NR$^1$, O, S or CONR$^1$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may be substituted by one or more radicals $R^1$, or a diarylamino group, diheteroarylamino group or arylheteroarylamino group having 10 to 40 aromatic ring atoms, which may be substituted by one or more radicals $R^1$; two or more adjacent radicals R here may also form a mono- or polycyclic, aliphatic, aromatic and/or benzo-fused ring system with one another;

$R^1$ is on each occurrence, identically or differently, H, D, F, Cl, Br, I, $N(R^2)_2$, CN, $NO_2$, $Si(R^2)_3$, $B(OR^2)_2$, C(=O)$R^2$, P(=O)$(R^2)_2$, S(=O)$R^2$, S(=O)$_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, C=NR$^2$, P(=O)($R^2$), SO, $SO_2$, NR$^2$, O, S or CONR$^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$; two or more adjacent radicals $R^1$ here may form a mono- or polycyclic, aliphatic or aromatic ring system with one another;

$R^2$ is on each occurrence, identically or differently, H, D, F or an aliphatic, aromatic and/or heteroaromatic organic radical having 1 to 20 C atoms, in particular a hydrocarbon radical, in which, in addition, one or more H atoms may be replaced by D or F; two or more substituents $R^2$ here may also form a mono- or polycyclic, aliphatic or aromatic ring system with one another;

L' is, identically or differently on each occurrence, any desired co-ligand;

anion is any desired anion;

n is 1, 2 or 3;

m is 0, 1, 2, 3 or 4;

w is 1, 2 or 3;

x, y, z are on each occurrence, identically or differently, 0, 1, 2 or 3, where $(w \cdot x)=(y \cdot z)$;

a plurality of ligands L here may also be linked to one another or L may be linked to L' via any desired bridge V and thus form a tridentate, tetradentate, pentadentate or hexadentate ligand system.

In the moiety of the formula (2) indicated above, an aromatic bond (bond order 1.5) may also be present in Cy2 between the group A and the adjacent group Y or between the two groups Y in Cy2 if Cy2 stands for an aryl or heteroaryl group.

The indices n and m here are selected so that the coordination number on the metal M corresponds overall, depending on the metal, to the usual coordination number for this metal. This is usually the coordination number 4, 5 or 6 for transition metals, depending on the metal. It is generally known that metal coordination compounds have different coordination numbers, i.e. bind a different number of ligands, depending on the metal and on the oxidation state of the metal. Since the preferred coordination numbers of metals and metal ions in various oxidation states belong to the general expert knowledge of the person skilled in the art in the area of organometallic chemistry or coordination chemistry, it is readily possible for the person skilled in the art to use a suitable number of ligands, depending on the metal and its oxidation state and depending on the precise structure of the ligand L, and thus to select the indices n and m suitably.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

The ligands may also bond to the metal via a carbene carbon atom. A cyclic carbene in the sense of this invention is a cyclic group which bonds to the metal via a neutral C atom. The cyclic group here may be saturated or unsaturated. Preference is given here to Arduengo carbenes, i.e. carbenes in which two nitrogen atoms are bonded to the carbene C atom. A five-membered Arduengo carbene ring or another unsaturated five-membered carbene ring is likewise regarded as being an aryl group for the purposes of this invention.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by a linear or cyclic alkylene group or by a silylene group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methyl-butyl, n-pentyl, s-pentyl, tert-pentyl, 2-pentyl, neopentyl, cyclopentyl, n-hexyl, s-hexyl, tert-hexyl, 2-hexyl, 3-hexyl, cyclohexyl, 2-methylpentyl, neohexyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo-[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3- thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds of the formula (1), characterised in that they are uncharged, i.e. are electrically neutral. This is achieved in a simple manner by selecting the charges of the ligands L and L' in such a way that they compensate for the charge of the complexed metal atom M. In a preferred embodiment of the invention, the indices x=y=z=0.

Preference is furthermore given to compounds of the formula (1), characterised in that the sum of the valence electrons around the metal atom is 16 in tetracoordinated complexes and 16 or 18 in pentacoordinated complexes and 18 in hexacoordinated complexes. This preference is due to the particular stability of these metal complexes.

In a preferred embodiment of the invention, M stands for a transition metal or for a main-group metal. If M stands for a main-group metal, it preferably stands for a metal from the third, fourth or fifth main group, in particular for tin.

Preference is given to compounds of the formula (1) in which M stands for a transition metal, in particular for a tetracoordinated, pentacoordinated or hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, platinum, copper and gold. Very particular preference is given to iridium and platinum. The metals here can be in various oxidation states. The above-mentioned metals are preferably in the oxidation states Cr(0), Cr(II), Cr(III), Cr(IV), Cr(VI), Mo(0), Mo(II), Mo(III), Mo(IV), Mo(VI), W(0), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V); very particular preference is given to Mo(0), W(0), Re(I), Ru(II), Os(II), Rh(III), Ir(III), Pt(II) and Cu(I), in particular Ir(III) and Pt(II).

In a preferred embodiment of the invention, M is a tetracoordinated metal, and the index n stands for 1 or 2. If the index n=1, one bidentate or two monodentate ligands L', preferably one bidentate ligand L', is (are) also coordinated to the metal M. If the index n=2, the index m=0.

In a further preferred embodiment of the invention, M is a hexacoordinated metal, and the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are also coordinated to the metal. If the index n=2, one bidentate or two monodentate ligands L', preferably one bidentate ligand L', is (are) also coordinated to the metal. If the index n=3, the index m=0.

The ligands L are bidentate ligands which bond to the metal M via one carbon atom and one nitrogen atom or via two carbon atoms or via two nitrogen atoms. In a preferred embodiment of the invention, the ligands L coordinate to the metal M via at least one carbon atom. The ligands L particularly preferably coordinate to the metal M via one carbon atom and one nitrogen atom or via two carbon atoms, one of which represents a carbene carbon atom. It is therefore preferred for one group A in the ligands L to stand for a nitrogen atom and for the other group A to stand for a carbon atom.

Cy1 in the moieties of the formula (2) is a six-membered or five-membered ring, where an aryl or heteroaryl group may also be condensed onto the six-membered ring. In a preferred embodiment of the invention, Cy1 contains one or two groups Z, particularly preferably precisely one group Z.

In a preferred embodiment of the invention, Cy1 is a six-membered, mono- or diunsaturated ring, i.e. the ring Cy1 particularly preferably has one or two double bonds. Cy1 in moieties of the formula (2) is then particularly preferably selected from the structures of the following formulae (3) to (21):

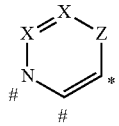

formula (3)

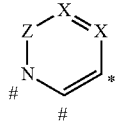

formula (4)

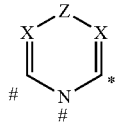

formula (5)

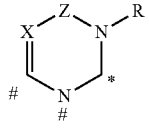

formula (6)

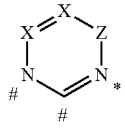

formula (7)

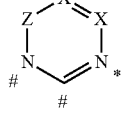

formula (8)

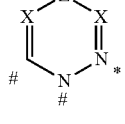

formula (9)

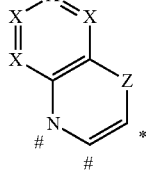

formula (10)

formula (11)
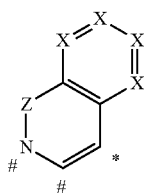

formula (12)
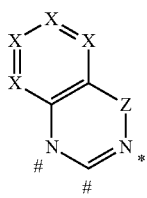

formula (13)
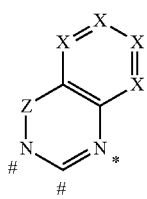

formula (14)
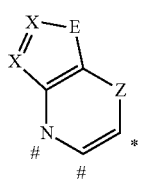

formula (15)
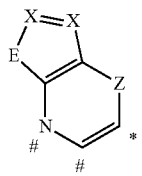

formula (16)
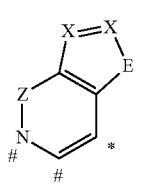

formula (17)
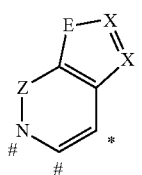

formula (18)
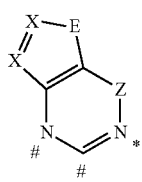

formula (19)
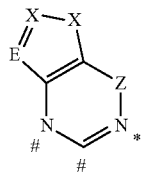

formula (20)
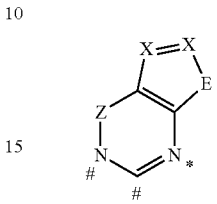

formula (21)
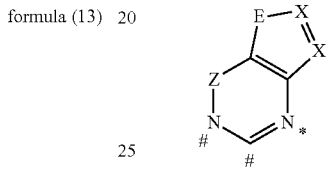

where E stands, identically or differently on each occurrence, for S, O or NR, and the other symbols used have the same meanings as stated above, and where * indicates the position of the coordination to the metal, and where # indicates the bond to Cy2 or to X in the ligand L.

In a further preferred embodiment of the invention, Cy1 is a five-membered, mono- or diunsaturated ring, i.e. the ring Cy1 preferably has one or two double bonds. Cy1 in moieties of the formula (2) is then particularly preferably selected from the structures of the following formulae (22) to (26):

formula (22)
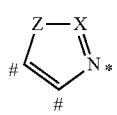

formula (23)
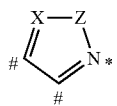

formula (24)
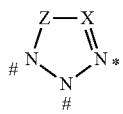

formula (25)
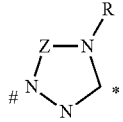

formula (26)
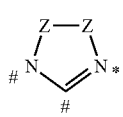

where the symbols used have the same meanings as stated above, and where * indicates the position of the coordination to the metal, and where # indicates the bond to Cy2 or to X in the ligand L.

In a further preferred embodiment of the invention, the ring Cy2 in moieties of the formula (2) is selected from structures of the formulae (3) to (26) indicated above or of the formulae (27) to (44) indicated below:

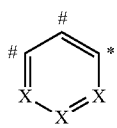
formula (27)

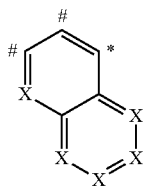
formula (28)

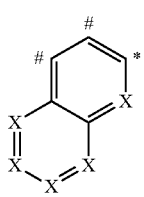
formula (29)

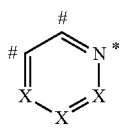
formula (30)

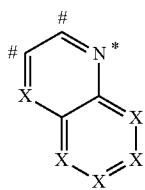
formula (31)

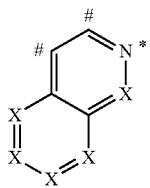
formula (32)

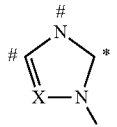
formula (33)

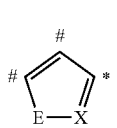
formula (34)

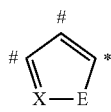
formula (35)

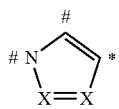
formula (36)

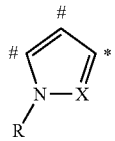
formula (37)

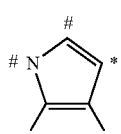
formula (38)

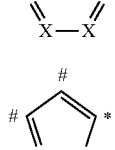
formula (39)

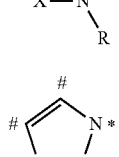
formula (40)

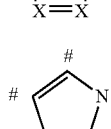
formula (41)

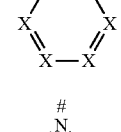
formula (42)

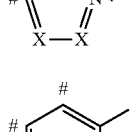
formula (43)

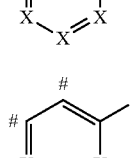
formula (44)

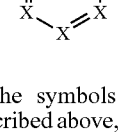

The symbols used here have the same meanings as described above, and preferably a maximum of three symbols X in each group stand for N, particularly preferably a maximum of two symbols X in each group stand for N, very particularly preferably a maximum of one symbol X in each group stands for N. Especially preferably, all symbols X stand for CR.

In a preferred embodiment of the invention, at least one group X in moieties of the formula (2) stands for CR. Particularly preferably, both groups X in moieties of the formula (2) stand for CR. This preference also applies if the preferred structures Cy1 of the formulae (3) to (26) indicated above and/or Cy2 of the formulae (3) to (44) are used.

In a further preferred embodiment of the invention, the group Z which is bonded in Cy1 in the moieties of the formula (2) and of the formulae (3) to (21) stands for C(=O), $CR_2$, NR, O or S. Z particularly preferably stands for C(=O) or $CR_2$, very particularly preferably for C(=O). Z in the moieties of the formulae (22) to (26) furthermore preferably stands for C(=O) or $CR_2$, particularly preferably for C(=O). If Z=$CR_2$, the two radicals R may then also form a ring system with one another and thus form a spiro system.

A particularly preferred embodiment of the moiety of the formula (2) is therefore the structure of the following formula (45):

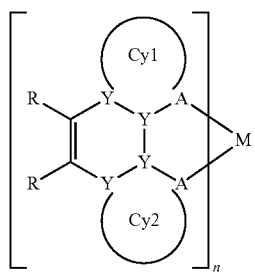

formula (45)

where Cy1 is selected from the structures of the formulae (3) to (26) indicated above, and Cy2 is selected from the structures of the formulae (3) to (44) indicated above. The other symbols and indices used have the meanings stated above, and Z in the formulae (3) to (21) is preferably selected from C(=O), $CR_2$, NR, O and S, and Z in the formulae (22) to (26) is preferably selected from C(=O) or $CR_2$.

In a particularly preferred embodiment of the invention, the ligand L in the moieties of the formulae (2) and (45) is built up from groups Cy1 of the formulae (3) to (26) indicated above and from groups Cy2 of the formulae (27) to (44) indicated above. Particularly preferred combinations are thus the combinations indicated in Table A below.

TABLE A

| No. | Cy1 | Cy2 |
|---|---|---|
| 1 | Formula (3) | Formula (27) |
| 2 | Formula (3) | Formula (28) |
| 3 | Formula (3) | Formula (29) |
| 4 | Formula (3) | Formula (30) |
| 5 | Formula (3) | Formula (31) |
| 6 | Formula (3) | Formula (32) |
| 7 | Formula (3) | Formula (33) |
| 8 | Formula (3) | Formula (34) |
| 9 | Formula (3) | Formula (35) |
| 10 | Formula (3) | Formula (36) |
| 11 | Formula (3) | Formula (37) |
| 12 | Formula (3) | Formula (38) |
| 13 | Formula (3) | Formula (39) |
| 14 | Formula (3) | Formula (40) |
| 15 | Formula (3) | Formula (41) |
| 16 | Formula (3) | Formula (42) |
| 17 | Formula (3) | Formula (43) |
| 18 | Formula (3) | Formula (44) |
| 19 | Formula (4) | Formula (27) |
| 20 | Formula (4) | Formula (28) |

TABLE A-continued

| No. | Cy1 | Cy2 |
|---|---|---|
| 21 | Formula (4) | Formula (29) |
| 22 | Formula (4) | Formula (30) |
| 23 | Formula (4) | Formula (31) |
| 24 | Formula (4) | Formula (32) |
| 25 | Formula (4) | Formula (33) |
| 26 | Formula (4) | Formula (34) |
| 27 | Formula (4) | Formula (35) |
| 28 | Formula (4) | Formula (36) |
| 29 | Formula (4) | Formula (37) |
| 30 | Formula (4) | Formula (38) |
| 31 | Formula (4) | Formula (39) |
| 32 | Formula (4) | Formula (40) |
| 33 | Formula (4) | Formula (41) |
| 34 | Formula (4) | Formula (42) |
| 35 | Formula (4) | Formula (43) |
| 36 | Formula (4) | Formula (44) |
| 37 | Formula (5) | Formula (27) |
| 38 | Formula (5) | Formula (28) |
| 39 | Formula (5) | Formula (29) |
| 40 | Formula (5) | Formula (30) |
| 41 | Formula (5) | Formula (31) |
| 42 | Formula (5) | Formula (32) |
| 43 | Formula (5) | Formula (33) |
| 44 | Formula (5) | Formula (34) |
| 45 | Formula (5) | Formula (35) |
| 46 | Formula (5) | Formula (36) |
| 47 | Formula (5) | Formula (37) |
| 48 | Formula (5) | Formula (38) |
| 49 | Formula (5) | Formula (39) |
| 50 | Formula (5) | Formula (40) |
| 51 | Formula (5) | Formula (41) |
| 52 | Formula (5) | Formula (42) |
| 53 | Formula (5) | Formula (43) |
| 54 | Formula (5) | Formula (44) |
| 55 | Formula (6) | Formula (27) |
| 56 | Formula (6) | Formula (28) |
| 57 | Formula (6) | Formula (29) |
| 58 | Formula (6) | Formula (30) |
| 59 | Formula (6) | Formula (31) |
| 60 | Formula (6) | Formula (32) |
| 61 | Formula (6) | Formula (33) |
| 62 | Formula (6) | Formula (34) |
| 63 | Formula (6) | Formula (35) |
| 64 | Formula (6) | Formula (36) |
| 65 | Formula (6) | Formula (37) |
| 66 | Formula (6) | Formula (38) |
| 67 | Formula (6) | Formula (39) |
| 68 | Formula (6) | Formula (40) |
| 69 | Formula (6) | Formula (41) |
| 70 | Formula (6) | Formula (42) |
| 71 | Formula (6) | Formula (43) |
| 72 | Formula (6) | Formula (44) |
| 73 | Formula (7) | Formula (27) |
| 74 | Formula (7) | Formula (28) |
| 75 | Formula (7) | Formula (29) |
| 76 | Formula (7) | Formula (30) |
| 77 | Formula (7) | Formula (31) |
| 78 | Formula (7) | Formula (32) |
| 79 | Formula (7) | Formula (33) |
| 80 | Formula (7) | Formula (34) |
| 81 | Formula (7) | Formula (35) |
| 82 | Formula (7) | Formula (36) |
| 83 | Formula (7) | Formula (37) |
| 84 | Formula (7) | Formula (38) |
| 85 | Formula (7) | Formula (39) |
| 86 | Formula (7) | Formula (40) |
| 87 | Formula (7) | Formula (41) |
| 88 | Formula (7) | Formula (42) |
| 89 | Formula (7) | Formula (43) |
| 90 | Formula (7) | Formula (44) |
| 91 | Formula (8) | Formula (27) |
| 92 | Formula (8) | Formula (28) |
| 93 | Formula (8) | Formula (29) |
| 94 | Formula (8) | Formula (30) |
| 95 | Formula (8) | Formula (31) |
| 96 | Formula (8) | Formula (32) |
| 97 | Formula (8) | Formula (33) |
| 98 | Formula (8) | Formula (34) |

TABLE A-continued

| No. | Cy1 | Cy2 |
|---|---|---|
| 99 | Formula (8) | Formula (35) |
| 100 | Formula (8) | Formula (36) |
| 101 | Formula (8) | Formula (37) |
| 102 | Formula (8) | Formula (38) |
| 103 | Formula (8) | Formula (39) |
| 104 | Formula (8) | Formula (40) |
| 105 | Formula (8) | Formula (41) |
| 106 | Formula (8) | Formula (42) |
| 107 | Formula (8) | Formula (43) |
| 108 | Formula (8) | Formula (44) |
| 109 | Formula (9) | Formula (27) |
| 110 | Formula (9) | Formula (28) |
| 111 | Formula (9) | Formula (29) |
| 112 | Formula (9) | Formula (30) |
| 113 | Formula (9) | Formula (31) |
| 114 | Formula (9) | Formula (32) |
| 115 | Formula (9) | Formula (33) |
| 116 | Formula (9) | Formula (34) |
| 117 | Formula (9) | Formula (35) |
| 118 | Formula (9) | Formula (36) |
| 119 | Formula (9) | Formula (37) |
| 120 | Formula (9) | Formula (38) |
| 121 | Formula (9) | Formula (39) |
| 122 | Formula (9) | Formula (40) |
| 123 | Formula (9) | Formula (41) |
| 124 | Formula (9) | Formula (42) |
| 125 | Formula (9) | Formula (43) |
| 126 | Formula (9) | Formula (44) |
| 127 | Formula (10) | Formula (27) |
| 128 | Formula (10) | Formula (28) |
| 129 | Formula (10) | Formula (29) |
| 130 | Formula (10) | Formula (30) |
| 131 | Formula (10) | Formula (31) |
| 132 | Formula (10) | Formula (32) |
| 133 | Formula (10) | Formula (33) |
| 134 | Formula (10) | Formula (34) |
| 135 | Formula (10) | Formula (35) |
| 136 | Formula (10) | Formula (36) |
| 137 | Formula (10) | Formula (37) |
| 138 | Formula (10) | Formula (38) |
| 139 | Formula (10) | Formula (39) |
| 140 | Formula (10) | Formula (40) |
| 141 | Formula (10) | Formula (41) |
| 142 | Formula (10) | Formula (42) |
| 143 | Formula (10) | Formula (43) |
| 144 | Formula (10) | Formula (44) |
| 145 | Formula (11) | Formula (27) |
| 146 | Formula (11) | Formula (28) |
| 147 | Formula (11) | Formula (29) |
| 148 | Formula (11) | Formula (30) |
| 149 | Formula (11) | Formula (31) |
| 150 | Formula (11) | Formula (32) |
| 151 | Formula (11) | Formula (33) |
| 152 | Formula (11) | Formula (34) |
| 153 | Formula (11) | Formula (35) |
| 154 | Formula (11) | Formula (36) |
| 155 | Formula (11) | Formula (37) |
| 156 | Formula (11) | Formula (38) |
| 157 | Formula (11) | Formula (39) |
| 158 | Formula (11) | Formula (40) |
| 159 | Formula (11) | Formula (41) |
| 160 | Formula (11) | Formula (42) |
| 161 | Formula (11) | Formula (43) |
| 162 | Formula (11) | Formula (44) |
| 163 | Formula (12) | Formula (27) |
| 164 | Formula (12) | Formula (28) |
| 165 | Formula (12) | Formula (29) |
| 166 | Formula (12) | Formula (30) |
| 167 | Formula (12) | Formula (31) |
| 168 | Formula (12) | Formula (32) |
| 169 | Formula (12) | Formula (33) |
| 170 | Formula (12) | Formula (34) |
| 171 | Formula (12) | Formula (35) |
| 172 | Formula (12) | Formula (36) |
| 173 | Formula (12) | Formula (37) |
| 174 | Formula (12) | Formula (38) |
| 175 | Formula (12) | Formula (39) |
| 176 | Formula (12) | Formula (40) |
| 177 | Formula (12) | Formula (41) |
| 178 | Formula (12) | Formula (42) |
| 179 | Formula (12) | Formula (43) |
| 180 | Formula (12) | Formula (44) |
| 181 | Formula (13) | Formula (27) |
| 182 | Formula (13) | Formula (28) |
| 183 | Formula (13) | Formula (29) |
| 184 | Formula (13) | Formula (30) |
| 185 | Formula (13) | Formula (31) |
| 186 | Formula (13) | Formula (32) |
| 187 | Formula (13) | Formula (33) |
| 188 | Formula (13) | Formula (34) |
| 189 | Formula (13) | Formula (35) |
| 190 | Formula (13) | Formula (36) |
| 191 | Formula (13) | Formula (37) |
| 192 | Formula (13) | Formula (38) |
| 193 | Formula (13) | Formula (39) |
| 194 | Formula (13) | Formula (40) |
| 195 | Formula (13) | Formula (41) |
| 196 | Formula (13) | Formula (42) |
| 197 | Formula (13) | Formula (43) |
| 198 | Formula (13) | Formula (44) |
| 199 | Formula (14) | Formula (27) |
| 200 | Formula (14) | Formula (28) |
| 201 | Formula (14) | Formula (29) |
| 202 | Formula (14) | Formula (30) |
| 203 | Formula (14) | Formula (31) |
| 204 | Formula (14) | Formula (32) |
| 205 | Formula (14) | Formula (33) |
| 206 | Formula (14) | Formula (34) |
| 207 | Formula (14) | Formula (35) |
| 208 | Formula (14) | Formula (36) |
| 209 | Formula (14) | Formula (37) |
| 210 | Formula (14) | Formula (38) |
| 211 | Formula (14) | Formula (39) |
| 212 | Formula (14) | Formula (40) |
| 213 | Formula (14) | Formula (41) |
| 214 | Formula (14) | Formula (42) |
| 215 | Formula (14) | Formula (43) |
| 216 | Formula (14) | Formula (44) |
| 217 | Formula (15) | Formula (27) |
| 218 | Formula (15) | Formula (28) |
| 219 | Formula (15) | Formula (29) |
| 220 | Formula (15) | Formula (30) |
| 221 | Formula (15) | Formula (31) |
| 222 | Formula (15) | Formula (32) |
| 223 | Formula (15) | Formula (33) |
| 224 | Formula (15) | Formula (34) |
| 225 | Formula (15) | Formula (35) |
| 226 | Formula (15) | Formula (36) |
| 227 | Formula (15) | Formula (37) |
| 228 | Formula (15) | Formula (38) |
| 229 | Formula (15) | Formula (39) |
| 230 | Formula (15) | Formula (40) |
| 231 | Formula (15) | Formula (41) |
| 232 | Formula (15) | Formula (42) |
| 233 | Formula (15) | Formula (43) |
| 234 | Formula (15) | Formula (44) |
| 235 | Formula (16) | Formula (27) |
| 236 | Formula (16) | Formula (28) |
| 237 | Formula (16) | Formula (29) |
| 238 | Formula (16) | Formula (30) |
| 239 | Formula (16) | Formula (31) |
| 240 | Formula (16) | Formula (32) |
| 241 | Formula (16) | Formula (33) |
| 242 | Formula (16) | Formula (34) |
| 243 | Formula (16) | Formula (35) |
| 244 | Formula (16) | Formula (36) |
| 245 | Formula (16) | Formula (37) |
| 246 | Formula (16) | Formula (38) |
| 247 | Formula (16) | Formula (39) |
| 248 | Formula (16) | Formula (40) |
| 249 | Formula (16) | Formula (41) |
| 250 | Formula (16) | Formula (42) |
| 251 | Formula (16) | Formula (43) |
| 252 | Formula (16) | Formula (44) |
| 253 | Formula (17) | Formula (27) |
| 254 | Formula (17) | Formula (28) |

TABLE A-continued

| No. | Cy1 | Cy2 |
|---|---|---|
| 255 | Formula (17) | Formula (29) |
| 256 | Formula (17) | Formula (30) |
| 257 | Formula (17) | Formula (31) |
| 258 | Formula (17) | Formula (32) |
| 259 | Formula (17) | Formula (33) |
| 260 | Formula (17) | Formula (34) |
| 261 | Formula (17) | Formula (35) |
| 262 | Formula (17) | Formula (36) |
| 263 | Formula (17) | Formula (37) |
| 264 | Formula (17) | Formula (38) |
| 265 | Formula (17) | Formula (39) |
| 266 | Formula (17) | Formula (40) |
| 267 | Formula (17) | Formula (41) |
| 268 | Formula (17) | Formula (42) |
| 269 | Formula (17) | Formula (43) |
| 270 | Formula (17) | Formula (44) |
| 271 | Formula (18) | Formula (27) |
| 272 | Formula (18) | Formula (28) |
| 273 | Formula (18) | Formula (29) |
| 274 | Formula (18) | Formula (30) |
| 275 | Formula (18) | Formula (31) |
| 276 | Formula (18) | Formula (32) |
| 277 | Formula (18) | Formula (33) |
| 278 | Formula (18) | Formula (34) |
| 279 | Formula (18) | Formula (35) |
| 280 | Formula (18) | Formula (36) |
| 281 | Formula (18) | Formula (37) |
| 282 | Formula (18) | Formula (38) |
| 283 | Formula (18) | Formula (39) |
| 284 | Formula (18) | Formula (40) |
| 285 | Formula (18) | Formula (41) |
| 286 | Formula (18) | Formula (42) |
| 287 | Formula (18) | Formula (43) |
| 288 | Formula (18) | Formula (44) |
| 289 | Formula (19) | Formula (27) |
| 290 | Formula (19) | Formula (28) |
| 291 | Formula (19) | Formula (29) |
| 292 | Formula (19) | Formula (30) |
| 293 | Formula (19) | Formula (31) |
| 294 | Formula (19) | Formula (32) |
| 295 | Formula (19) | Formula (33) |
| 296 | Formula (19) | Formula (34) |
| 297 | Formula (19) | Formula (35) |
| 298 | Formula (19) | Formula (36) |
| 299 | Formula (19) | Formula (37) |
| 300 | Formula (19) | Formula (38) |
| 301 | Formula (19) | Formula (39) |
| 302 | Formula (19) | Formula (40) |
| 303 | Formula (19) | Formula (41) |
| 304 | Formula (19) | Formula (42) |
| 305 | Formula (19) | Formula (43) |
| 306 | Formula (19) | Formula (44) |
| 307 | Formula (20) | Formula (27) |
| 308 | Formula (20) | Formula (28) |
| 309 | Formula (20) | Formula (29) |
| 310 | Formula (20) | Formula (30) |
| 311 | Formula (20) | Formula (31) |
| 312 | Formula (20) | Formula (32) |
| 313 | Formula (20) | Formula (33) |
| 314 | Formula (20) | Formula (34) |
| 315 | Formula (20) | Formula (35) |
| 316 | Formula (20) | Formula (36) |
| 317 | Formula (20) | Formula (37) |
| 318 | Formula (20) | Formula (38) |
| 319 | Formula (20) | Formula (39) |
| 320 | Formula (20) | Formula (40) |
| 321 | Formula (20) | Formula (41) |
| 322 | Formula (20) | Formula (42) |
| 323 | Formula (20) | Formula (43) |
| 324 | Formula (20) | Formula (44) |
| 325 | Formula (21) | Formula (27) |
| 326 | Formula (21) | Formula (28) |
| 327 | Formula (21) | Formula (29) |
| 328 | Formula (21) | Formula (30) |
| 329 | Formula (21) | Formula (31) |
| 330 | Formula (21) | Formula (32) |
| 331 | Formula (21) | Formula (33) |
| 332 | Formula (21) | Formula (34) |
| 333 | Formula (21) | Formula (35) |
| 334 | Formula (21) | Formula (36) |
| 335 | Formula (21) | Formula (37) |
| 336 | Formula (21) | Formula (38) |
| 337 | Formula (21) | Formula (39) |
| 338 | Formula (21) | Formula (40) |
| 339 | Formula (21) | Formula (41) |
| 340 | Formula (21) | Formula (42) |
| 341 | Formula (21) | Formula (43) |
| 342 | Formula (21) | Formula (44) |
| 343 | Formula (22) | Formula (27) |
| 344 | Formula (22) | Formula (28) |
| 345 | Formula (22) | Formula (29) |
| 346 | Formula (22) | Formula (30) |
| 347 | Formula (22) | Formula (31) |
| 348 | Formula (22) | Formula (32) |
| 349 | Formula (22) | Formula (33) |
| 350 | Formula (22) | Formula (34) |
| 351 | Formula (22) | Formula (35) |
| 352 | Formula (22) | Formula (36) |
| 353 | Formula (22) | Formula (37) |
| 354 | Formula (22) | Formula (38) |
| 355 | Formula (22) | Formula (39) |
| 356 | Formula (22) | Formula (40) |
| 357 | Formula (22) | Formula (41) |
| 358 | Formula (22) | Formula (42) |
| 359 | Formula (22) | Formula (43) |
| 360 | Formula (22) | Formula (44) |
| 361 | Formula (23) | Formula (27) |
| 362 | Formula (23) | Formula (28) |
| 363 | Formula (23) | Formula (29) |
| 364 | Formula (23) | Formula (30) |
| 365 | Formula (23) | Formula (31) |
| 366 | Formula (23) | Formula (32) |
| 367 | Formula (23) | Formula (33) |
| 368 | Formula (23) | Formula (34) |
| 369 | Formula (23) | Formula (35) |
| 370 | Formula (23) | Formula (36) |
| 371 | Formula (23) | Formula (37) |
| 372 | Formula (23) | Formula (38) |
| 373 | Formula (23) | Formula (39) |
| 374 | Formula (23) | Formula (40) |
| 375 | Formula (23) | Formula (41) |
| 376 | Formula (23) | Formula (42) |
| 377 | Formula (23) | Formula (43) |
| 378 | Formula (23) | Formula (44) |
| 379 | Formula (24) | Formula (27) |
| 380 | Formula (24) | Formula (28) |
| 381 | Formula (24) | Formula (29) |
| 382 | Formula (24) | Formula (30) |
| 383 | Formula (24) | Formula (31) |
| 384 | Formula (24) | Formula (32) |
| 385 | Formula (24) | Formula (33) |
| 386 | Formula (24) | Formula (34) |
| 387 | Formula (24) | Formula (35) |
| 388 | Formula (24) | Formula (36) |
| 389 | Formula (24) | Formula (37) |
| 390 | Formula (24) | Formula (38) |
| 391 | Formula (24) | Formula (39) |
| 392 | Formula (24) | Formula (40) |
| 393 | Formula (24) | Formula (41) |
| 394 | Formula (24) | Formula (42) |
| 395 | Formula (24) | Formula (43) |
| 396 | Formula (24) | Formula (44) |
| 397 | Formula (25) | Formula (27) |
| 398 | Formula (25) | Formula (28) |
| 399 | Formula (25) | Formula (29) |
| 400 | Formula (25) | Formula (30) |
| 401 | Formula (25) | Formula (31) |
| 402 | Formula (25) | Formula (32) |
| 403 | Formula (25) | Formula (33) |
| 404 | Formula (25) | Formula (34) |
| 405 | Formula (25) | Formula (35) |
| 406 | Formula (25) | Formula (36) |
| 407 | Formula (25) | Formula (37) |
| 408 | Formula (25) | Formula (38) |
| 409 | Formula (25) | Formula (39) |
| 410 | Formula (25) | Formula (40) |

TABLE A-continued

| No. | Cy1 | Cy2 |
|---|---|---|
| 411 | Formula (25) | Formula (41) |
| 412 | Formula (25) | Formula (42) |
| 413 | Formula (25) | Formula (43) |
| 414 | Formula (25) | Formula (44) |
| 415 | Formula (26) | Formula (27) |
| 416 | Formula (26) | Formula (28) |
| 417 | Formula (26) | Formula (29) |
| 418 | Formula (26) | Formula (30) |
| 419 | Formula (26) | Formula (31) |
| 420 | Formula (26) | Formula (32) |
| 421 | Formula (26) | Formula (33) |
| 422 | Formula (26) | Formula (34) |
| 423 | Formula (26) | Formula (35) |
| 424 | Formula (26) | Formula (36) |
| 425 | Formula (26) | Formula (37) |
| 426 | Formula (26) | Formula (38) |
| 427 | Formula (26) | Formula (39) |
| 428 | Formula (26) | Formula (40) |
| 429 | Formula (26) | Formula (41) |
| 430 | Formula (26) | Formula (42) |
| 431 | Formula (26) | Formula (43) |
| 432 | Formula (26) | Formula (44) |

For each of the combinations in Table 1, it is preferred for X on each occurrence, identically or differently, to be CR and for Z to be equal to C(=O) or CR$_2$.

Furthermore, larger condensed structures are possible through ring formation of the substituents. For example, structures of the following formulae (46) and (47) are thereby obtainable:

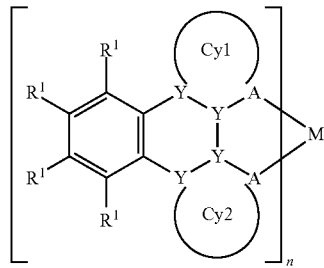

formula (46)

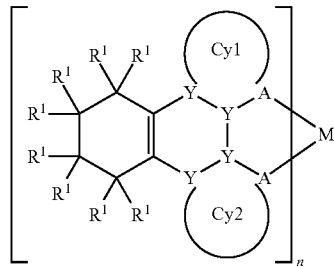

formula (47)

where the symbols and indices used have the meanings given above. R$^1$ in the formulae (46) and (47) preferably stands for H, D or an alkyl group having 1 to 5 C atoms, in particular for H or methyl.

The formulae (46) and (47) show merely by way of example how corresponding larger condensed ring systems are accessible through ring formation. Ring formation with the other structures according to the invention, for example with the moieties of the formulae (3) to (44), is possible entirely analogously.

It is furthermore possible for one of the substituents R in the moieties of the formulae (3) to (26) or (27) to (44) to represent a coordinating group which likewise coordinates to the metal M. Preferred coordinating groups R are aryl or heteroaryl groups, for example phenyl or pyridyl, aryl or alkyl cyanides, aryl or alkyl isocyanides, amines or amides, alcohols or alcoholates, thioalcohols or thioalcoholates, phosphines, phosphites, carbonyl functions, carboxylates, carbamides or aryl- or alkylacetylides. The moieties M(L)$_n$ of the following formulae (48) and (49), for example, are accessible here:

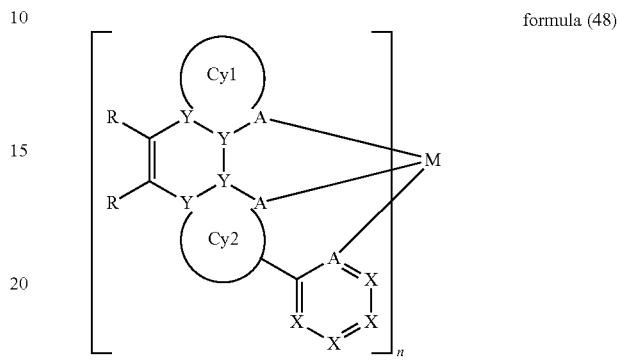

formula (48)

formula (49)

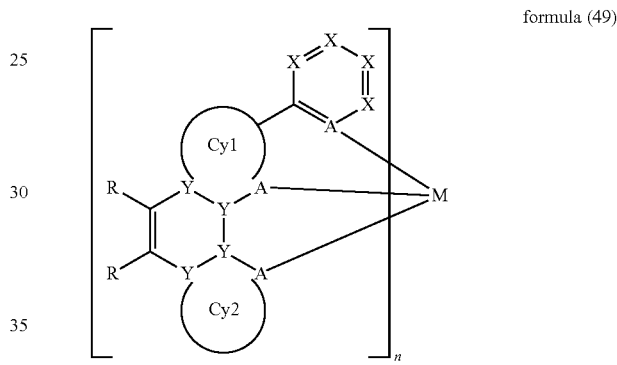

where the symbols and indices used have the meanings given above. Further structures containing tridentate or tetradentate ligands are also possible entirely analogously to these structures.

It is likewise possible for an aryl or heteroaryl group which is condensed onto Cy1 to be bonded to M directly or via a substituent R. Preferred coordinating groups R are O$^-$, S$^-$, N(R$^1$)$^-$, N(R$^1$)$_2$, P(R$^1$)$^-$ or P(R$^1$)$_2$. The moieties M(L)$_n$ of the following formula (50), for example, are accessible here:

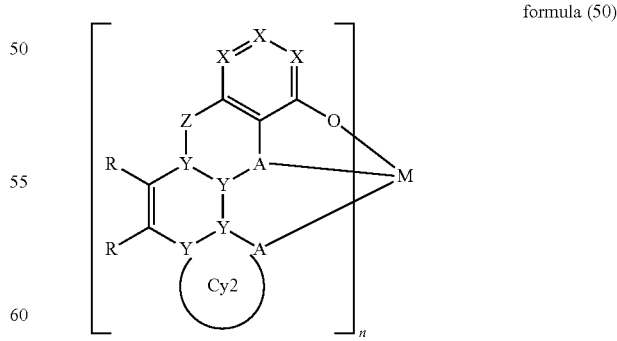

formula (50)

As described above, a bridging unit V which links this ligand L to one or more further ligands L or L' may also be present instead of one of the radicals R in formula (2). In a preferred embodiment of the invention, a bridging unit V is present instead of one of the radicals R, so that the ligands have a tridentate or polydentate or polypodal character. It is also possible for two such bridging units V to be present. This results in the formation of macrocyclic ligands or in the formation of cryptates.

Preferred structures containing polydentate ligands are the metal complexes of the following formulae (51) to (55):

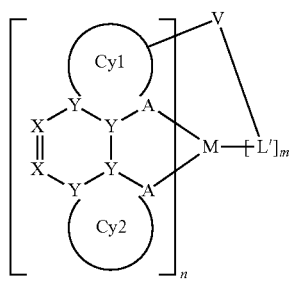

formula (51)

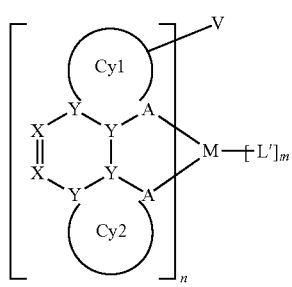

formula (52)

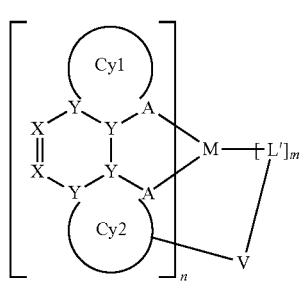

formula (53)

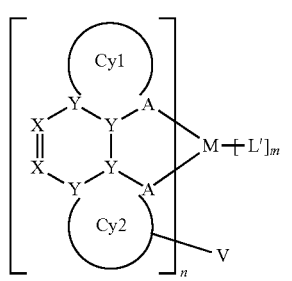

formula (54)

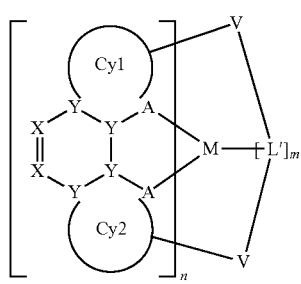

formula (55)

where the symbols used have the meanings given above, and V preferably represents a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or covalently bonds L to L'. The bridging unit V here may also be substituted by one or more radicals $R^1$. Furthermore, the bridging unit V may also have an asymmetrical structure, i.e. the linking of V to L and L' need not be identical. The bridging unit V can be neutral, singly, doubly or triply negatively charged or singly, doubly or triply positively charged. V is preferably neutral or singly negatively charged or singly positively charged. The charge of V is preferably selected so that overall a neutral complex forms.

If V bridges three ligands L to one another or two ligands L to L' or one ligand L to two ligands L', V is preferably selected, identically or differently on each occurrence, from the group consisting of B, $B(R^1)^-$, $B(C(R^1)_2)_3$, $(R^1)B(C(R^1)_2)_3^-$, $B(O)_3$, $(R^1)B(O)_3^-$, $B(C(R^1)_2C(R^1)_2)_3$, $(R^1)B(C(R^1)_2C(R^1)_2)_3^-$, $B(C(R^1)_2O)_3$, $(R^1)B(C(R^1)_2O)_3^-$, $B(OC(R^1)_2)_3$, $(R^1)B(OC(R^1)_2)_3^-$, $C(R^1)$, $CO^-$, $CN(R^1)_2$, $(R^1)C(C(R^1)_2)_3$, $(R^1)C(O)_3$, $(R^1)C(C(R^1)_2C(R^1)_2)_3$, $(R^1)C(C(R^1)_2O)_3$, $(R^1)C(OC(R^1)_2)_3$, $(R^1)C(Si(R^1)_2)_3$, $(R^1)C(Si(R^1)_2C(R^1)_2)_3$, $(R^1)C(C(R^1)_2Si(R^1)_2)_3$, $(R^1)C(Si(R^1)_2Si(R^1)_2)_3$, $Si(R^1)$, $(R^1)Si(C(R^1)_2)_3$, $(R^1)Si(O)_3$, $(R^1)Si(C(R^1)_2C(R^1)_2)_3$, $(R^1)Si(OC(R^1)_2)_3$, $(R^1)Si(C(R^1)_2O)_3$, $(R^1)Si(Si(R^1)_2)_3$, $(R^1)Si(Si(R^1)_2)C(R^1)_2)_3$, $(R^1)Si(C(R^1)_2Si(R^1)_2)_3$, $(R^1)Si(Si(R^1)_2Si(R^1)_2)_3$, N, NO, $N(R^1)^+$, $N(C(R^1)_2)_3$, $(R^1)N(C(R^1)_2)_3^+$, $N(C=O)_3$, $N(C(R^1)_2C(R^1)_2)_3$, $(R^1)N(C(R^1)_2C(R^1)_2)_3^+$, P, $P(R^1)^+$, PO, PS, PSe, PTe, $P(O)_3$, $PO(O)_3$, $P(OC(R^1)_2)_3$, $PO(OC(R^1)_2)_3$, $P(C(R^1)_2)_3$, $P(R^1)(C(R^1)_2)_3^+$, $PO(C(R^1)_2)_3$, $P(C(R^1)_2C(R^1)_2)_3$, $P(R^1)(C(R^1)_2C(R^1)_2)_3^+$, $PO(C(R^1)_2C(R^1)_2)_3$, $S^+$, $S(C(R^1)_2)_3^+$, $S(C(R^1)_2C(R^1)_2)_3^+$,
or a unit of the formula (56), (57), (58) or (59):

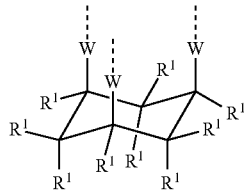

formula (56)

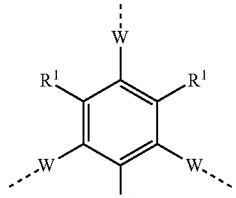

formula (57)

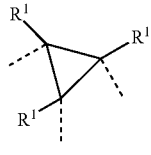

formula (58)

formula (59)

where the dashed bonds in each case indicate the bond to the part-ligands L or L', and W is selected, identically or differently on each occurrence, from the group consisting of a single bond, O, S, S(=O), S(=O)$_2$, NR$^1$, PR$^1$, P(=O)R$^1$, P(=NR$^1$), C(R$^1$)$_2$, C(=O), C(=NR$^1$), C(=C(R$^1$)$_2$), Si(R$^1$)$_2$ or BR$^1$. The other symbols used have the meanings given above.

If V bridges two ligands L to one another or one ligand L to L', V is preferably selected, identically or differently on each occurrence, from the group consisting of BR$^1$, B(R$^1$)$_2^-$, C(R$^1$)$_2$, C(=O), Si(R$^1$)$_2$, NR$^1$, PR$^1$, P(R$^1$)$_2^+$, P(=O)(R$^1$), P(=S)(R$^1$), AsR$^1$, As(=O)(R$^1$), As(=S)(R$^1$), O, S, Se, or a unit of the formulae (60) to (69):

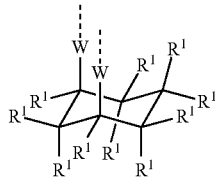
formula (60)

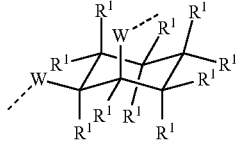
formula (61)

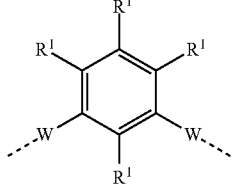
formula (62)

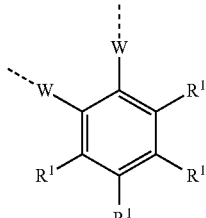
formula (63)

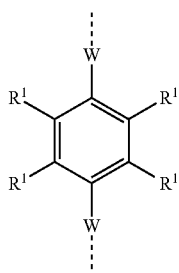
formula (64)

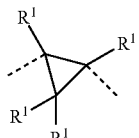
formula (65)

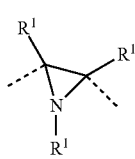
formula (66)

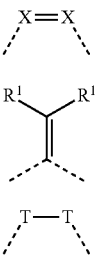

formula (67)

formula (68)

formula (69)

where the dashed bonds in each case indicate the bond to the part-ligands L or L', T stands on each occurrence, identically or differently, for C(R$^1$)$_2$, N(R$^1$), O or S, and the other symbols used each have the meanings indicated above.

Preferred ligands L' as occur in formula (1) are described below. The ligand groups L' can also be selected correspondingly if they are bonded to L via a bridging unit V.

The ligands L' are preferably neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' can also be bonded to L via a bridging group V.

Preferred neutral, monodentate ligands L' are selected from carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides F$^-$, Cl$^-$, Br$^-$ and I$^-$, alkylacetylides, such as, for example, methyl-C≡C$^-$, tert-butyl-C≡C$^-$, arylacetylides, such as, for example, phenyl-C≡C$^-$, cyanide, cyanate, isocyanate, thiocyanate, isothiocyanate, aliphatic or aromatic alcoholates, such as, for example, methanolate, ethanolate, propanolate, iso-propanolate, tert-butylate, phenolate, aliphatic or aromatic thioalcoholates, such as, for example, methanethiolate, ethanethiolate, propanethiolate, iso-propanethiolate, tert-thiobutylate, thiophenolate, amides, such as, for example, dimethylamide, diethylamide, di-iso-propylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably C$_1$-C$_{20}$-alkyl groups, particularly preferably C$_1$-C$_{10}$-alkyl groups, very particularly preferably C$_1$-C$_4$-alkyl groups. An aryl group is also taken to mean heteroaryl groups. These groups are as defined above.

Preferred di- or trianionic ligands are $O^{2-}$, $S^{2-}$, carbides, which result in coordination in the form R—C≡M, and nitrenes, which result in coordination in the form R—N=M, where R generally stands for a substituent, and $N^{3-}$.

Preferred neutral or mono- or dianionic, bidentate or polydentate ligands L' are selected from diamines, such as, for example, ethylenediamine, N,N,N',N'-tetramethylethylenediamine, propylenediamine, N,N,N',N'-tetra-methylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-di-iso-propylphenylimino)ethyl]pyridine, 2-[1-(methylimino)ethyl]-pyridine, 2-[1-(ethylimino)ethyl]pyridine, 2-[1-(iso-propylimino) ethyl]pyridine, 2-[1-(tert-butylimino)ethyl]pyridine, diimines, such as, for example, 1,2-bis(methylimino)ethane, 1,2-bis(ethylimino)ethane, 1,2-bis(iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tert-butylimino)butane, 1,2-bis(phenylimino)ethane, 1,2-bis(2-methylphenylimino)ethane, 1,2-bis(2,6-di-iso-propylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-di-iso-propylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis (diphenylphosphino)methane, bis(diphenylphosphino) ethane, bis(diphenylphosphino)propane, bis(diphenylphosphino)butane, bis(dimethylphosphino)methane, bis (dimethylphosphino)ethane, bis(dimethylphosphino) propane, bis(diethylphosphino)methane, bis (diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 2,2,6, 6-tetramethyl-3,5-heptanedione, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl) borate and tetrakis(1-pyrazolyl)borate.

Preference is furthermore given to bidentate monoanionic ligands L', which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals R. A multiplicity of ligands of this type is known to the person skilled in the art in the area of phosphorescent electroluminescent devices, and he will be able, without inventive step, to select further ligands of this type as ligand L' for compounds of the formula (1). The combination of two groups as depicted by the following formulae (70) to (97) is generally particularly suitable for this purpose, where one group is bonded via a neutral nitrogen atom or a carbene atom and the other group is bonded via a negatively charged carbon atom or a negatively charged nitrogen atom. The ligand L' can then be formed from the groups of the formulae (70) to (97) through these groups bonding to one another in each case at the position denoted by #. The position at which the groups coordinate to the metal is denoted by *. These groups may also be bonded to the ligand L via one or two bridging units V.

formula (70)

formula (71)

formula (72)

formula (73)

formula (74)

formula (75)

formula (76)

formula (77)

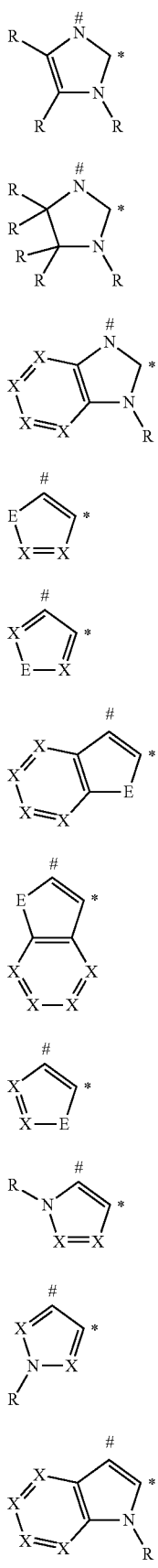
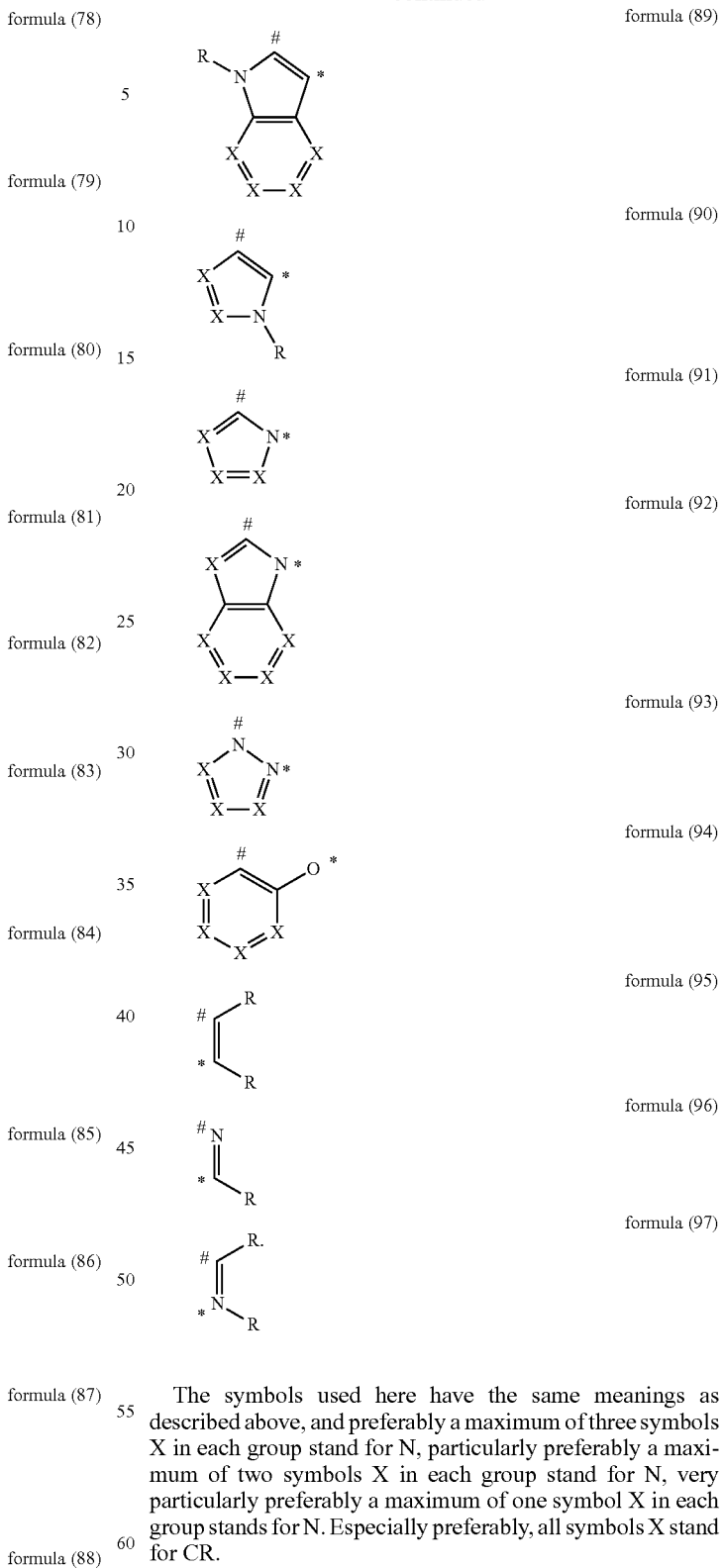

The symbols used here have the same meanings as described above, and preferably a maximum of three symbols X in each group stand for N, particularly preferably a maximum of two symbols X in each group stand for N, very particularly preferably a maximum of one symbol X in each group stands for N. Especially preferably, all symbols X stand for CR.

Likewise preferred ligands L' are $\eta^5$-cyclopentadienyl, $\eta^5$-pentamethylcyclopentadienyl, $\eta^6$-benzene or $\eta^7$-cycloheptatrienyl, each of which may be substituted by one or more radicals $R^1$.

Likewise preferred ligands L' are 1,3,5-cis-cyclohexane derivatives, in particular of the formula (98), 1,1,1-tri(methylene)methane derivatives, in particular of the formula (99), and 1,1,1-trisubstituted methanes, in particular of the formulae (100) and (101):

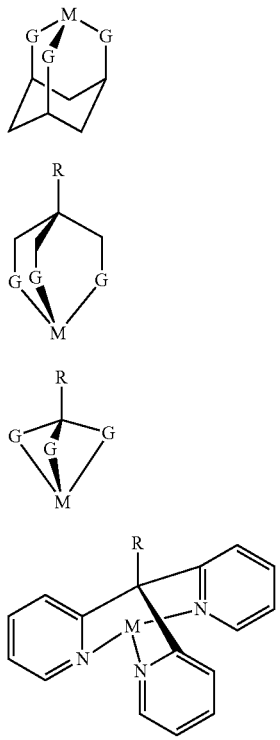

formula (98)

formula (99)

formula (100)

formula (101)

where the coordination to the metal M is shown in each of the formulae, R has the meaning given above, and G stands, identically or differently on each occurrence, for $O^-$, $S^-$, $COO^-$, $P(R^1)_2$ or $N(R^1)_2$.

Preferred radicals R in the structures shown above of the formulae (2) to (55) and (70) to (101), which are present as substituents on X, are selected on each occurrence, identically or differently, from the group consisting of H, D, F, Br, $N(R^1)_2$, CN, $B(OR^1)_2$, $C(=O)R^1$, $P(=O)(R^1)_2$, a straight-chain alkyl group having 1 to 10 C atoms or a straight-chain alkenyl group having 2 to 10 C atoms or a branched or cyclic alkyl, alkenyl or alkynyl group having 3 to 10 C atoms, each of which may be substituted by one or more radicals $R^1$, where one or more H atoms may be replaced by D, F or CN, or an aromatic or heteroaromatic ring system having 5 to 14 aromatic ring atoms, which may in each case be substituted by one or more radicals $R^1$; a plurality of adjacent radicals R here may also form a mono- or polycyclic, aliphatic, aromatic and/or benzo-fused ring system with one another. Particularly preferred radicals R are selected on each occurrence, identically or differently, from the group consisting of H, F, Br, CN, $B(OR^1)_2$, a straight-chain alkyl group having 1 to 5 C atoms, in particular methyl, or a branched or cyclic alkyl group having 3 to 5 C atoms, in particular isopropyl or tert-butyl, where one or more H atoms may be replaced by F, or an aromatic or heteroaromatic ring system having 5 to 12 aromatic ring atoms, which may in each case be substituted by one or more radicals $R^1$; a plurality of adjacent radicals R here may also form a mono- or polycyclic, aliphatic, aromatic and/or benzo-fused ring system with one another.

The complexes according to the invention can be facial or pseudofacial or they can be meridional or pseudomeridional.

The preferred embodiments indicated above can be combined with one another as desired. In a particularly preferred embodiment of the invention, the preferred embodiments indicated above apply simultaneously.

The metal complexes according to the invention can in principle be prepared by various processes. However, the processes described below have proven particularly suitable.

The present invention therefore furthermore relates to a process for the preparation of the metal complex compounds of the formula (1) by reaction of the corresponding free ligands with metal alkoxides of the formula (102), with metal ketoketonates of the formula (103), with metal halides of the formula (104) or with dimeric metal complexes of the formula (105):

$M(OR^1)_n$      formula (102)

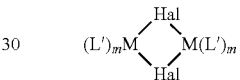

formula (103)

$MHal_n$      formula (104)

formula (105)

$(L')_mM\begin{smallmatrix}Hal\\\\Hal\end{smallmatrix}M(L')_m$ where the symbols and indices M, L', m, n and $R^1$ have the meanings indicated above, and Hal=F, Cl, Br or I.

It is likewise possible to use metal compounds, in particular iridium compounds, which carry both alkoxide and/or halide and/or hydroxyl radicals as well as ketoketonate radicals. These compounds may also be charged. Corresponding iridium compounds which are particularly suitable as starting materials are disclosed in WO 04/085449. $[IrCl_2(acac)_2]^-$, for example $Na[IrCl_2(acac)_2]$, is particularly suitable. Further particularly suitable iridium starting materials are iridium (III) tris(acetylacetonate) and indium(III) tris(2,2,6,6-tetramethyl-3,5-heptanedionate).

The synthesis of the complexes is preferably carried out as described in WO 02/060910 and in WO 04/085449. Heteroleptic complexes can also be synthesised, for example, in accordance with WO 05/042548. The synthesis here can also be activated, for example, thermally, photochemically and/or by microwave radiation.

For the preparation of homoleptic iridium complexes, the ligand is preferably reacted with $Na[IrCl_2(acac)_2]$ or $Ir(acac)_3$ in the melt or in an inert solvent, such as, for example, polyalcohols (ethylene glycol, glycerol, etc.), polyether alcohols (di-, tri- or tetraethylene glycol) or polyethers (di-, tri-, tetra- or polyethylene glycol dimethyl ether), at temperatures of 80 to 350° C. A ratio of the ligand to the iridium compound of 1:3 to 1:100, preferably 1:4-1:10, is used here.

For the preparation of heteroleptic iridium complexes, the procedure in accordance with Scheme 1 can be followed. Firstly, reaction of the ligands with a suitable Ir precursor, preferably indium(III) chloride hydrate, in the presence of a protic solvent or solvent mixture gives the chloro-bridged dimeric iridium complexes, which are then reacted further with one or more ligands, optionally with addition of additives, such as bases or salts (WO 2007/065523).

Scheme 1:

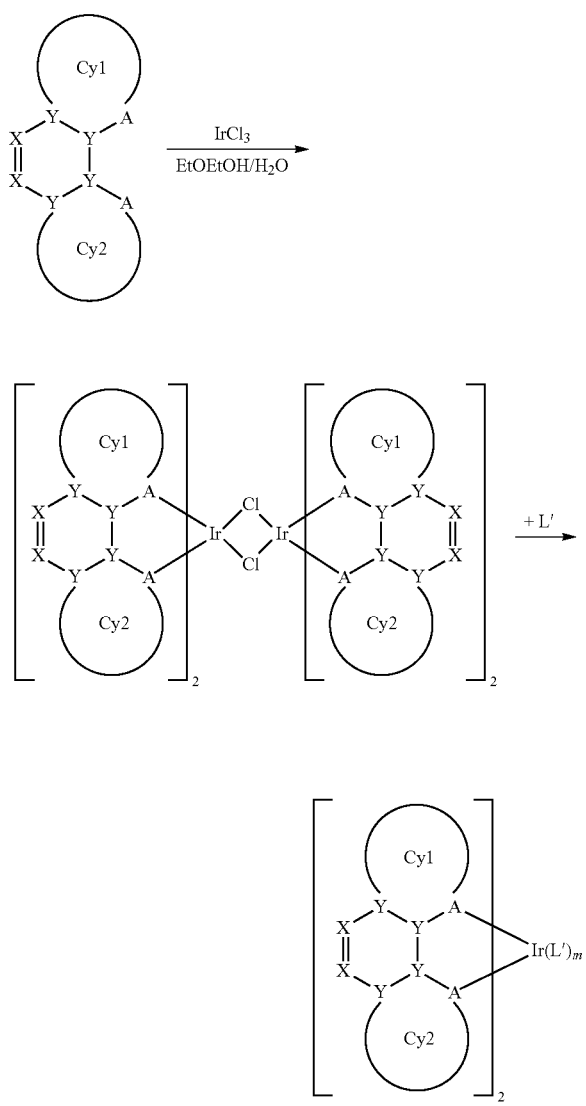

The preparation of heteroleptic iridium complexes containing a ligand according to the invention can be carried out entirely analogously (Scheme 2).

Scheme 2:

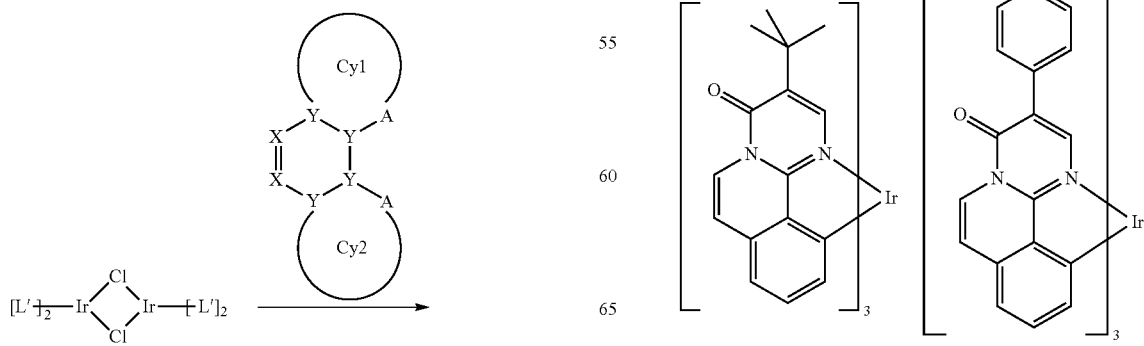

These processes enable the compounds of the formula (1) according to the invention to be obtained in high purity, preferably greater than 99% (determined by means of $^1$H-NMR and/or HPLC).

The synthetic methods explained here enable the preparation of, inter alia, the structures according to the invention depicted below.

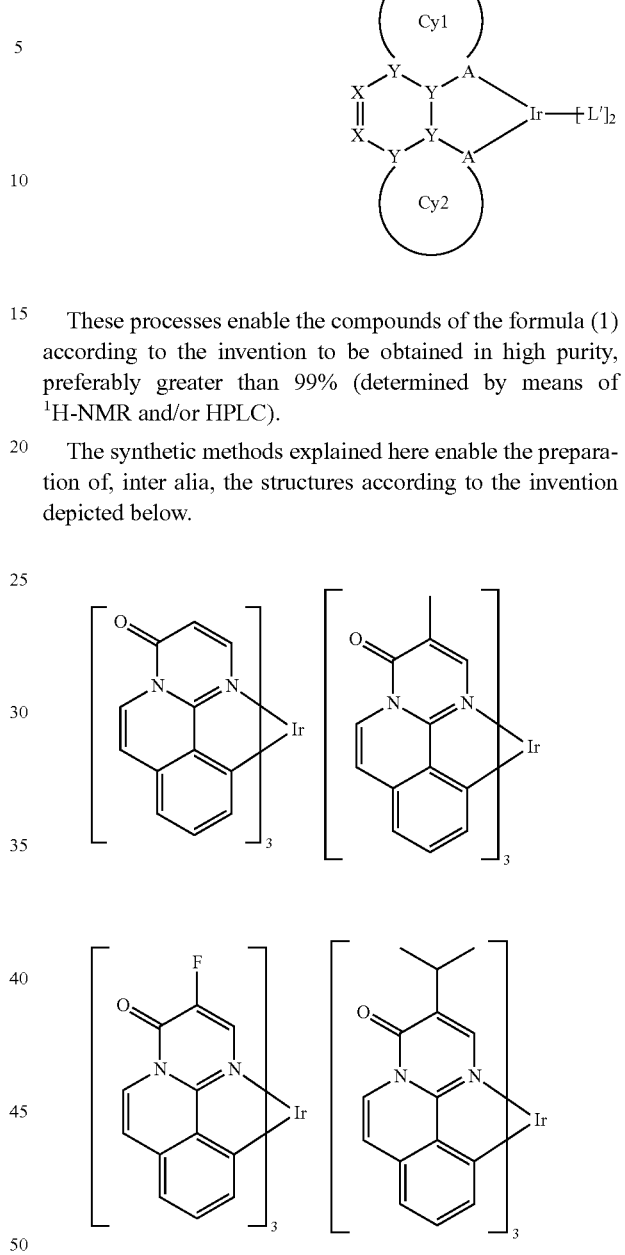

31
-continued
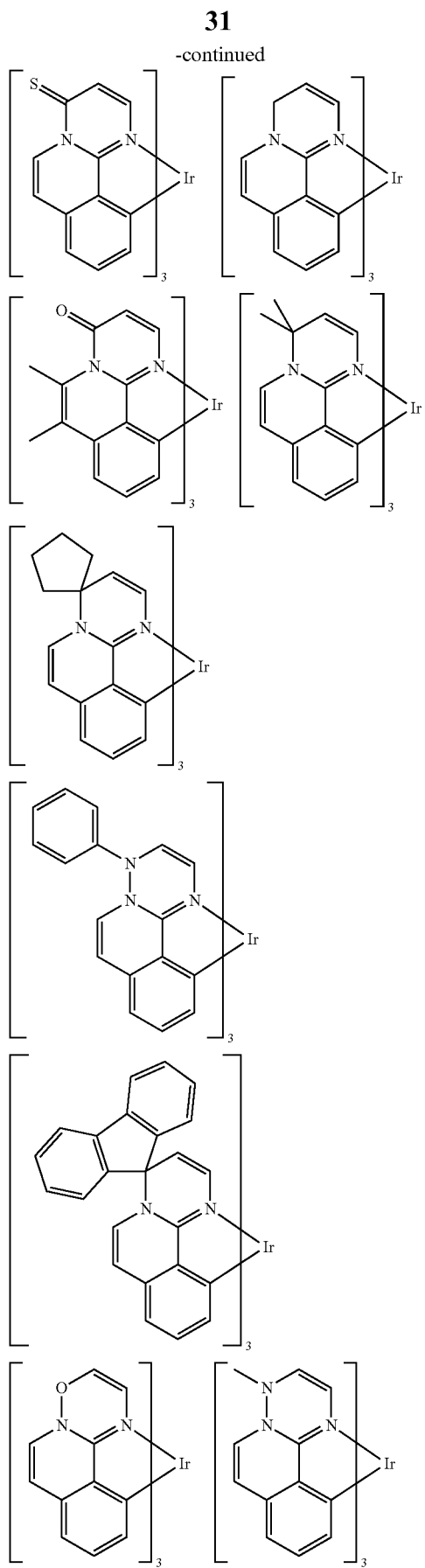
32
-continued
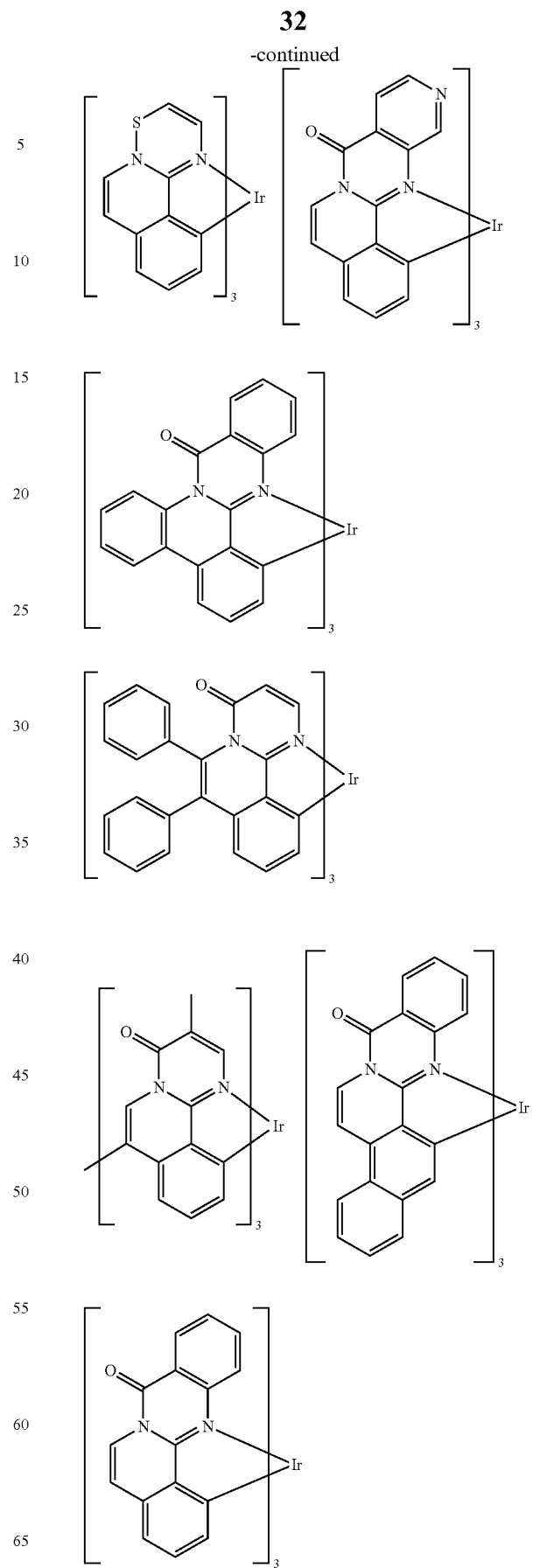

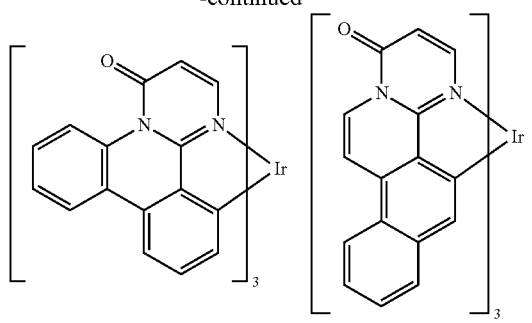
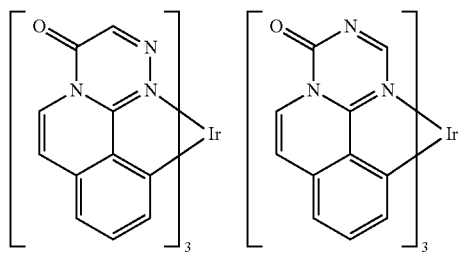
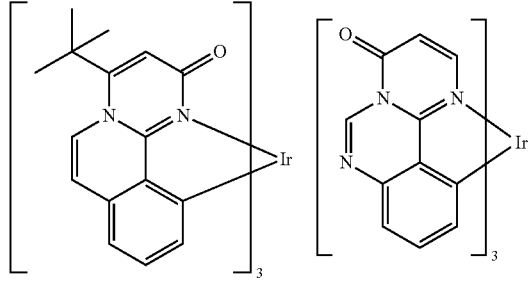
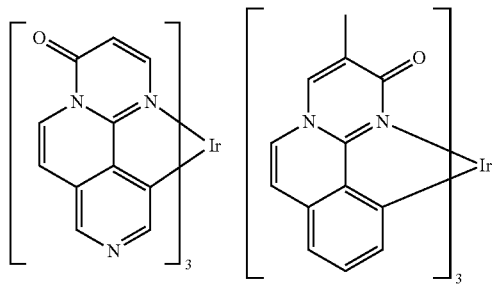
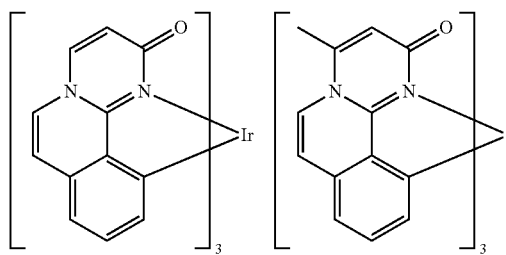
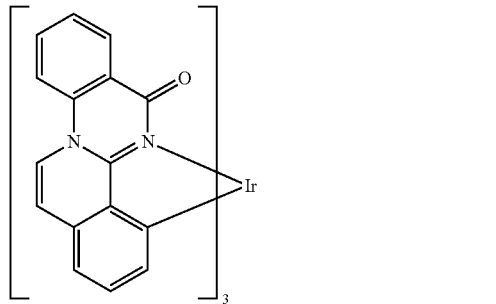
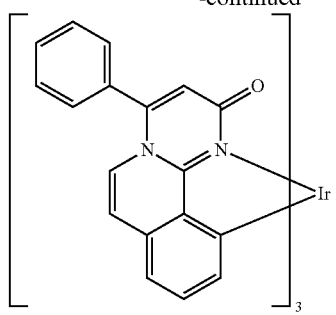
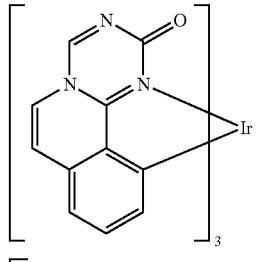
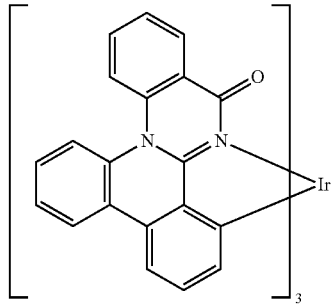
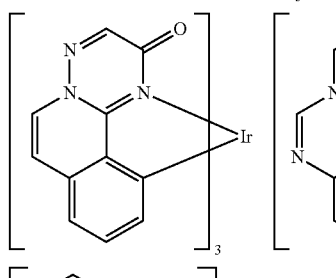
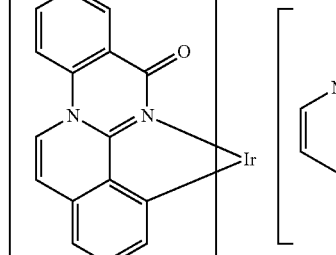
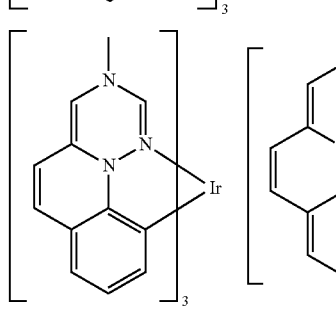

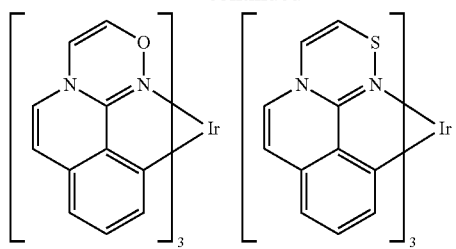
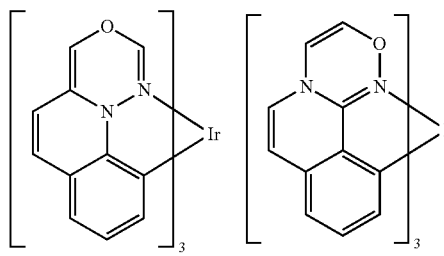
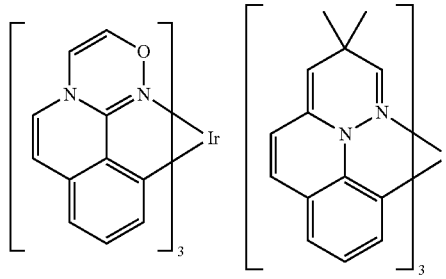
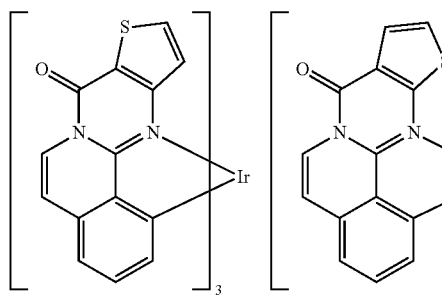
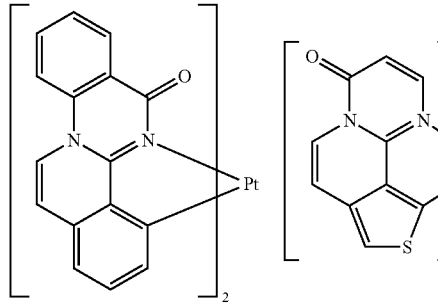
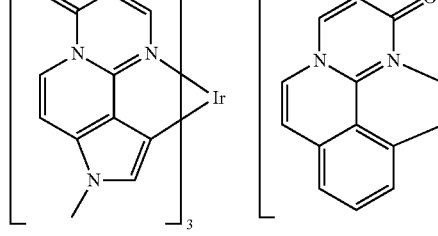
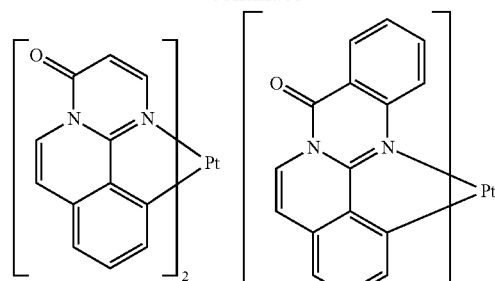
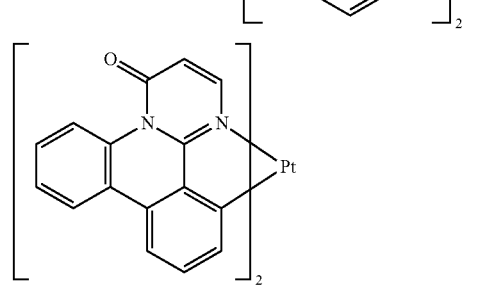
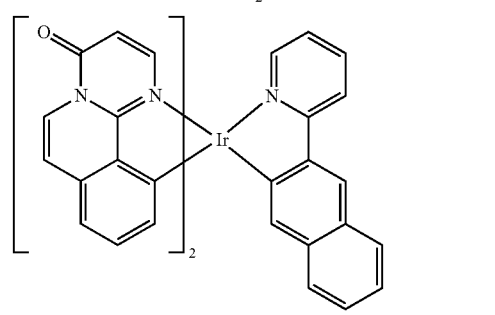
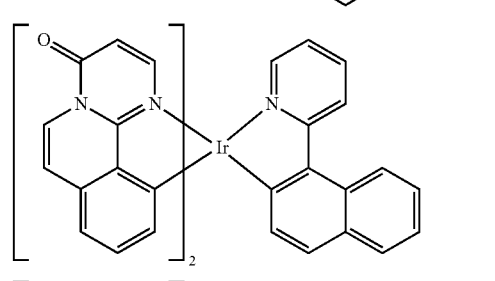
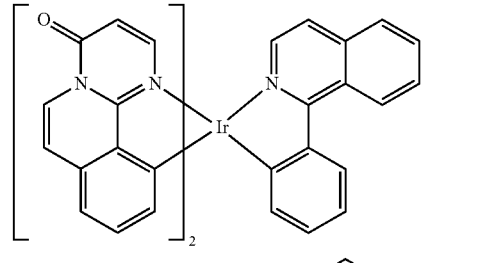
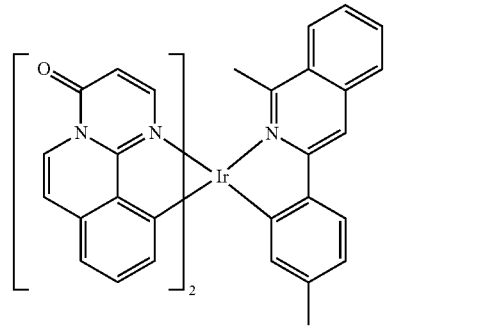

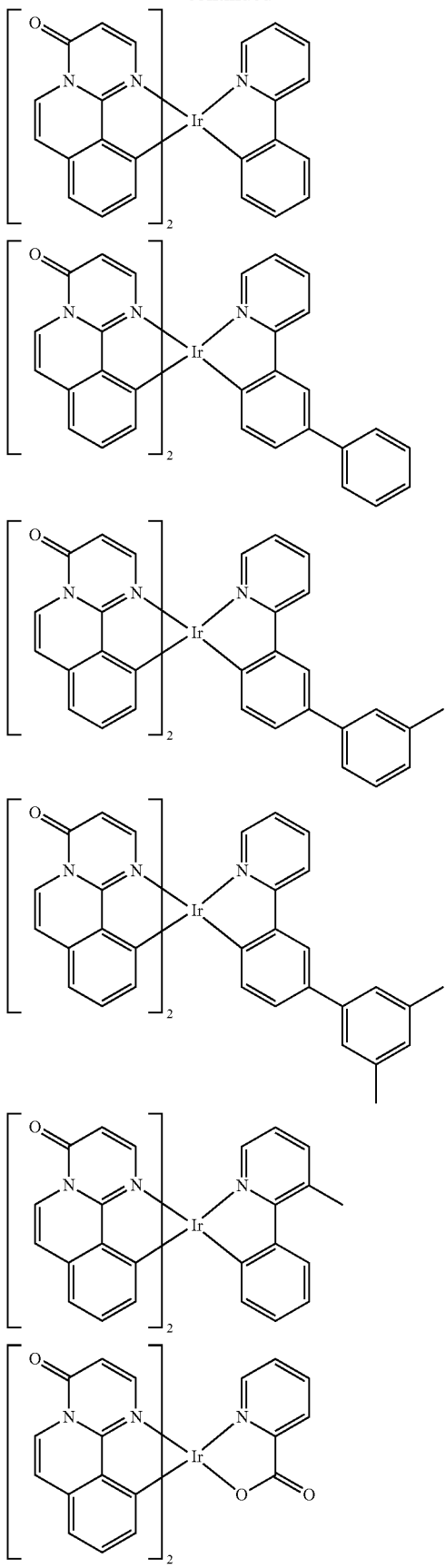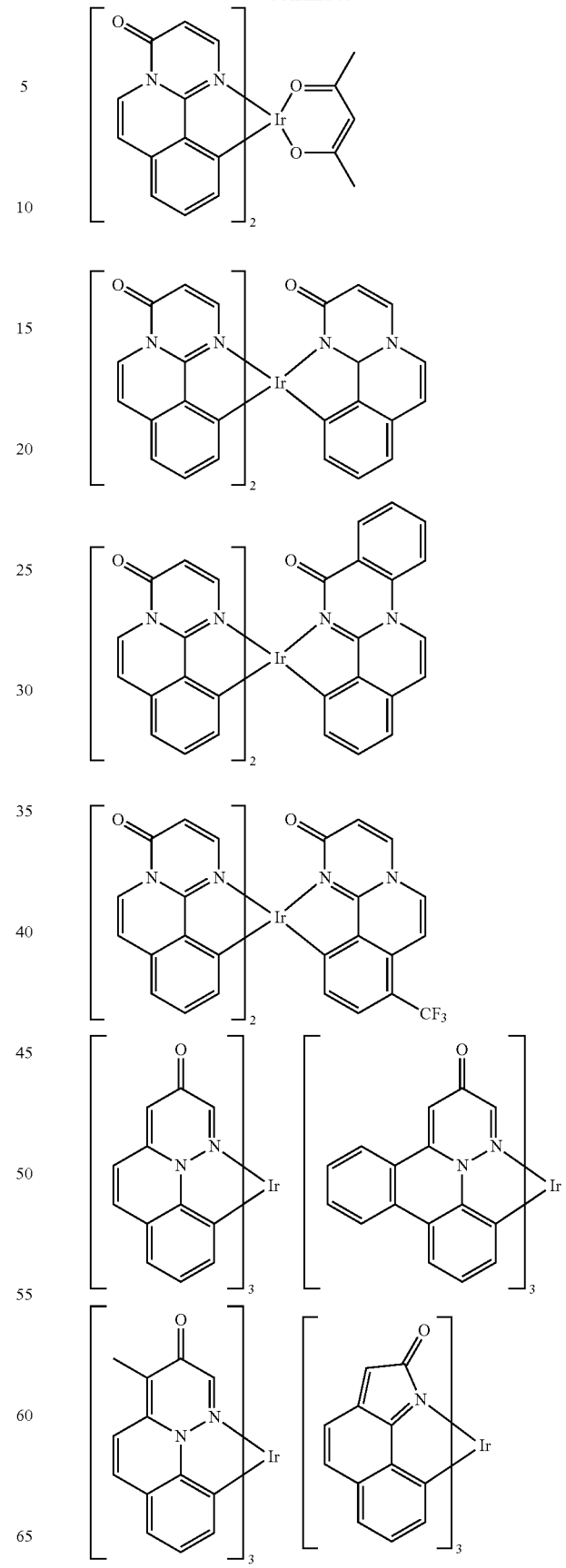

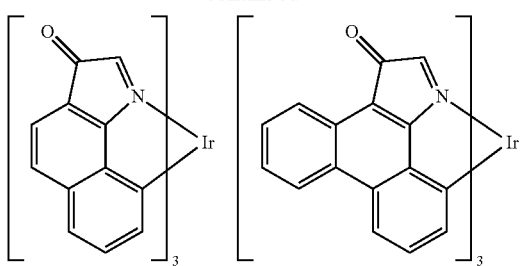

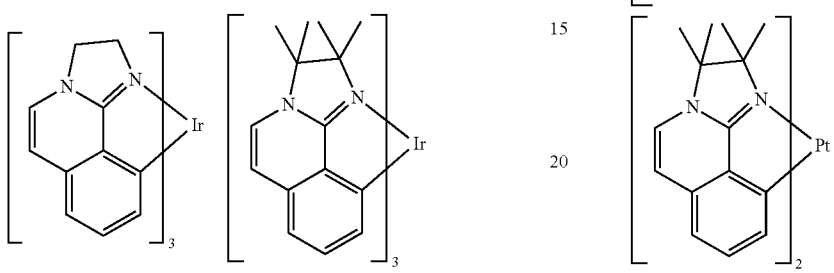

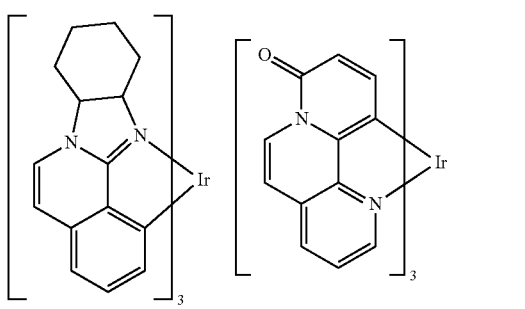

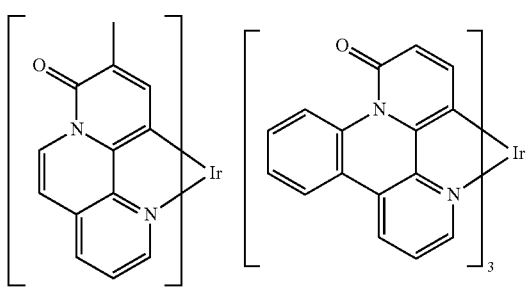

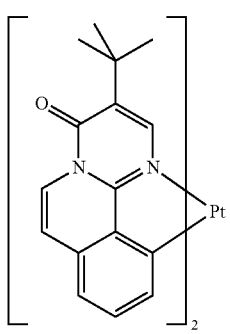

The compounds according to the invention described above can also be used as recurring units in conjugated, partially conjugated or non-conjugated oligomers, polymers or dendrimers. For the purposes of this invention, an oligomer is taken to mean a compound having about 3 to 10 recurring units, which may be identical or different. The polymerisation here is preferably carried out via a bromine or boronic acid functionality. Thus, compounds of this type can be copolymerised, inter alia, into polyfluorenes (for example in accordance with EP 842208 or WO 00/22026), polyspirobifluorenes (for example in accordance with EP 707020 or EP 894107), polydihydrophenanthrenes (for example in accordance with WO 05/014689), polyindenofluorenes (for example in accordance with WO 04/041901 and WO 04/113468), polyphenanthrenes (for example in accordance with WO 05/104264), poly-para-phenylenes (for example in accordance with WO 92/18552), polycarbazoles (for example in accordance with WO 04/070772 or WO 04/113468), polyketones (for example in accordance with WO 05/040302), polysilanes (for example in accordance with WO 05/111113) or polythiophenes (for example in accordance with EP 1028136) or also into copolymers which comprise various of these units. They can either be incorporated into the side chain or into the main chain of the polymer here or can also represent branching points of the polymer chains (for example in accordance with WO 06/003000).

The invention thus furthermore relates to conjugated, partially conjugated or non-conjugated oligomers, polymers or dendrimers comprising one or more of the compounds of the formula (1), where at least one of the radicals R defined above represents a bond to the polymer or dendrimer. For units of the formula (1), the same preferences as already described above apply in polymers and dendrimers. Apart from the units mentioned above, the oligomers, polymers or dendrimers may comprise further units selected, for example, from recurring units which have hole-transport properties or electron-transport properties. The materials known from the prior art are suitable for this purpose.

The oligomers, polymers, copolymers and dendrimers mentioned above are distinguished by good solubility in organic solvents and high efficiency and stability in organic electroluminescent devices.

The compounds of the formula (1) according to the invention, in particular those which are functionalised by halogens, may furthermore also be further functionalised by common reaction types and thus converted into extended compounds of the formula (1). An example which may be mentioned here is functionalisation with arylboronic acids by the Suzuki method or with amines by the Hartwig-Buchwald method.

The complexes of the formula (1) described above or the preferred embodiments indicated above can be used as active component in an electronic device. The present invention therefore furthermore relates to the use of a compound of the formula (1) or in accordance with one of the preferred embodiments in an electronic device.

The present invention still furthermore relates to an electronic device comprising at least one compound of the formula (1) or according to one of the preferred embodiments.

An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (see, for example, WO 05/011013), or systems which have more than three emitting layers.

In a preferred embodiment of the invention, the organic electroluminescent device comprises the compound of the formula (1) or the preferred embodiments indicated above as emitting compound in one or more emitting layers.

If the compound of the formula (1) is employed as emitting compound in an emitting layer, it is preferably employed in combination with one or more matrix materials. The mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula (1), based on the mixture as a whole comprising emitter and matrix material. Correspondingly, the mixture comprises between 99 and 1% by vol., preferably between 98 and 10% by vol., particularly preferably between 97 and 60% by vol., especially between 95 and 85% by vol., of the matrix material or materials, based on the mixture as a whole comprising emitter and matrix material.

Suitable matrix materials for the compounds according to the invention are ketones, phosphine oxides, sulfoxides and sulfones, for example in accordance with WO 04/013080, WO 04/093207, WO 06/005627 or WO 10/006,680, triarylamines, carbazole derivatives, for example CBP (N,N-bis-carbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056, 746, indenocarbazole derivatives, for example in accordance with the unpublished applications DE 102009023155.2 and DE 102009031021.5, azacarbazoles, for example in accordance with EP 1617710, EP 1617711, EP 1731584, JP 2005/347160, bridged carbazole derivatives, such as, for example, in accordance with US 2009/0136779 or WO 10/050,778, bipolar matrix materials, for example in accordance with WO 07/137,725, silanes, for example in accordance with WO 05/111172, azaboroles or boronic esters, for example in accordance with WO 06/117052, triazine derivatives, for example in accordance with WO 10/015,306, WO 07/063, 754 or WO 08/056,746, zinc complexes, for example in accordance with EP 652273 or in accordance with WO 09/062,578, diaza- or tetraazasilole derivatives, for example in accordance with WO 10/054,729, or diazaphosphole derivatives, for example in accordance with WO 10/054,730.

It may also be preferred to employ a plurality of different matrix materials as a mixture, in particular at least one electron-conducting matrix material and at least one hole-conducting matrix material. A preferred combination is, for example, the use of an aromatic ketone or a triazine derivative with a triarylamine derivative or a carbazole derivative as mixed matrix for the metal complex according to the invention.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, Li$_2$O, BaF$_2$, MgO, NaF, CsF, Cs$_2$CO$_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent in order either to facilitate irradiation of the organic material (O-SCs) or the coupling-out of light (OLEDs/PLEDs, O-LASERs). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air. Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished by the following surprising advantages over the prior art:

1. Organic electroluminescent devices comprising compounds of the formula (1) as emitting materials have a very good lifetime.
2. Organic electroluminescent devices comprising compounds of the formula (1) as emitting materials have very good efficiency.
3. The metal complexes according to the invention give access to organic electroluminescent devices which phosphoresce in the red, orange, yellow, green and blue-green colour regions.
4. The metal complexes according to the invention and the ligands necessary for this purpose are accessible in a synthetically simple manner and in high yields.

These advantages mentioned above are not accompanied by an impairment of the other electronic properties.

The invention is explained in greater detail by the following examples, without wishing to restrict it thereby. The person skilled in the art will be able to synthesise further compounds according to the invention and use these in electronic devices on the basis of the descriptions without inventive step and will thus be able to carry out the invention throughout the range disclosed.

EXAMPLES

The following syntheses are carried out, unless indicated otherwise, under a protective-gas atmosphere in dried solvents with exclusion of light. The solvents and reagents can be purchased from ALDRICH or ABCR. The synthesis of ligands 1 to 5 is carried out in accordance with H. Reimlinger et al., Chem. Ber. 1972, 105, 108, that of ligand 6 is carried out in accordance with R. F. Cookson et al., J. Chem. Soc., Perkin Trans 1, 1975, 19, 1854, that of ligand 7 is carried out in accordance with T. A. Kuz'menko et al., Khimiya Geterotsiklicheskikh Soedinenii (1976), (12), 1666-71.

Ligand 1:

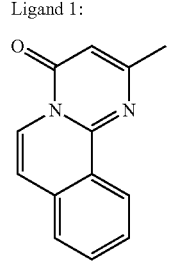

Ligand 2:

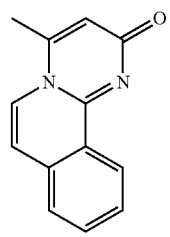

Ligand 3:

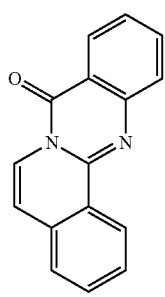

Ligand 4:

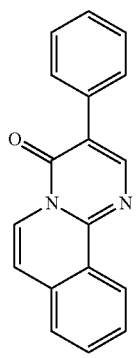

Ligand 5:

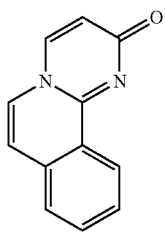

Ligand 6:

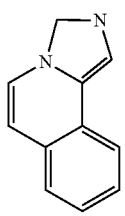

Ligand 7:

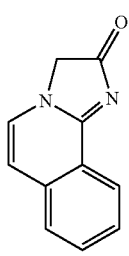

1) General Synthesis of Tris-Facial Iridium Complexes

A mixture of 6 parts of the ligand with one part of trisacetylacetonatoiridium(III) is stirred in an evacuated, sealed ampoule for the stated time at the stated temperature. After cooling, the glass-like melt is broken apart and comminuted, two parts by volume of THF are added, the mixture is stirred vigorously at room temperature for 1 h, and four parts by volume of methanol are then added dropwise. After stirring for 2 h, the yellow solid is filtered off, washed with methanol, dried, recrystallised from dichloroethane or chlorobenzene and then optionally sublimed in vacuo ($p=1\times10^{-5}$ mbar). Purity >99.5% or >99.9% according to HPLC.

| Ex. | Ligand | Ir complex | Reaction time Reaction temp. | Yield |
|---|---|---|---|---|
| 1 | 1 | | 48 h 250° C. | 55% |
| 2 | 2 | | 48 h 250° C. | 22% |
| 3 | 3 | | 72 h 250° C. | 68% |
| 4 | 4 | | 72 h 250° C. | 46% |
| 5 | 5 | | 120 h 250° C. | 17% |

-continued

| Ex. | Ligand | Ir complex | Reaction time Reaction temp. | Yield |
|---|---|---|---|---|
| 6 | 6 | [structure] | 60 h 230° C. | 21% |
| 7 | 7 | [structure] | 90 h 230° C. | 36% |

2) Heteroleptic Iridium Complexes:

Variant A:

Step 1:

A mixture of 10 mmol of sodium bisacetylacetonatodichloroiridate(III) [770720-50-8] and 24 mmol of ligand L is melted in a 50 ml glass ampoule in vacuo ($10^{-3}$ mbar). The ampoule is heated at the stated temperature for the stated time, during which the molten mixture is stirred with the aid of a magnetic stirrer. After cooling (ATTENTION: the ampoules are usually under pressure!), the ampoule is opened, the sinter cake is stirred for 3 h with 100 g of glass beads (diameter 3 mm) in 100 ml of the suspension medium indicated and mechanically digested in the process. The fine suspension is decanted off from the glass beads, the solid is filtered off with suction and dried in vacuo.

Step 2:

The crude chloro-bridged dimer of the formula $[Ir(L)_2Cl]_2$ obtained in this way is suspended in a mixture of 75 ml of 2-ethoxyethanol and 25 ml of water, 13 mmol of co-ligand CL or the co-ligand compound CL and 15 mmol of sodium carbonate are added. After 20 h under reflux, a further 75 ml of water are added dropwise, the mixture is cooled, the solid is filtered off with suction, washed three times with 50 ml of water each time and three times with 50 ml of methanol each time and dried in vacuo. The dry solid is placed in a hot extractor on an aluminium oxide bed (aluminium oxide, basic, activity grade 1) with a depth of 10 cm and then extracted with the stated extractant (amount about 500 ml). When the extraction is complete, the extractant is concentrated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated; when a purity of 99.5-99.9% has been reached, the metal complex is heated or sublimed. The heating is carried out in a high vacuum (p about $10^{-6}$ mbar) in the temperature range 200-300° C. The sublimation is carried out in a high vacuum (p about $10^{-6}$ mbar) in the temperature range from about 300 to about 390° C., with the sublimation preferably being carried out in the form of a fractional sublimation.

| Ex. | Ligand L | Co-ligand CL | Ir complex Step 1: reaction temp./ reaction time/ suspension medium Step 2: extractant | Yield |
|---|---|---|---|---|
| 8 | 3 | [structure] 123-54-6 CL1 | [structure] | 32% 250° C./40 h/DCM THF |

| Ex. | Ligand L | Co-ligand CL | Ir complex Step 1: reaction temp./reaction time/suspension medium Step 2: extractant | Yield |
|---|---|---|---|---|
| 9 | 4 | 123-54-6 CL1 | 250° C./60 h/DCM THF | 34% |

Variant B:

Step 1:
See Variant A, Step 1.

Step 2:
The crude chloro-bridged dimer of the formula $[Ir(L)_2Cl]_2$ obtained in this way is suspended in 1000 ml of dichloromethane and 150 ml of ethanol, 40 mmol of silver(I) trifluoromethanesulfonate are added to the suspension, and the mixture is stirred at room temperature for 24 h. The precipitated solid (AgCl) is filtered off with suction via a short Celite bed, and the filtrate is evaporated to dryness in vacuo. The solid obtained in this way is taken up in 100 ml of ethanol, 30 mmol of co-ligand CL are added, and the mixture is heated under reflux for 30 h. After cooling, the solid is filtered off with suction, washed twice with 50 ml of ethanol each time and dried in vacuo. The solid obtained in this way is placed in a hot extractor on an aluminium oxide bed (aluminium oxide, basic, activity grade 1) with a depth of 10 cm and then extracted with the stated extractant (amount about 500 ml). When the extraction is complete, the extractant is concentrated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated; when a purity of 99.5-99.9% has been reached, the metal complex is heated or sublimed. The heating is carried out in a high vacuum (p about $10^{-6}$ mbar) in the temperature range 200-300° C. The sublimation is carried out in a high vacuum (p about $10^{-6}$ mbar) in the temperature range from about 300 to about 390° C., with the sublimation preferably being carried out in the form of a fractional sublimation. In the case of ionic metal complexes, aluminium oxide is replaced by Celite in the hot-extraction step.

| Ex. | Ligand L | Co-ligand CL | Ir complex Step 1: reaction temp./reaction time/suspension medium Step 2: extractant | Yield |
|---|---|---|---|---|
| 10 | 3 | 1008-89-5 CL2 | 260° C./60 h/DCM THF | 36% |

| Ex. | Ligand L | Co-ligand CL | Ir complex Step 1: reaction temp./ reaction time/ suspension medium Step 2: extractant | Yield |
|---|---|---|---|---|
| 11 | 3 | 883-93-2 CL3 | 260° C./40 h/DCM THF | 27% |

3) Heteroleptic Platinum Complexes

A mixture of 10 mmol of platinum(II) chloride, 12 mmol of ligand L and 1 mmol of tetra-n-butylammonium chloride in 30 ml of dichloromethane is heated under reflux for 12 h. After dropwise addition of 100 ml of methanol, the fine solid is filtered off with suction, washed twice with 25 ml of methanol and dried in vacuo. The crude chloro-bridged dimer of the formula $[Pt(L)Cl]_2$ obtained in this way is suspended in a mixture of 60 ml of 2-ethoxyethanol and 20 ml of water, and 12 mmol of co-ligand CL or co-ligand compound CL and 12 mmol of sodium carbonate are added. After 20 h under reflux, a further 100 ml of water are added dropwise, the mixture is cooled, the solid is filtered off with suction, washed three times with 50 ml of water each time and three times with 50 ml of methanol each time and dried in vacuo. The solid obtained in this way is placed in a hot extractor on a Celite bed with a depth of 10 cm and then extracted with the stated extractant (amount about 500 ml). When the extraction is complete, the extractant is concentrated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated; when a purity of 99.5-99.9% has been reached, the metal complex is heated or sublimed. The heating is carried out in a high vacuum (p about $10^{-6}$ mbar) in the temperature range 200-300° C. The sublimation is carried out in a high vacuum (p about $10^{-6}$ mbar) in the temperature range from about 300 to about 390° C., with the sublimation preferably being carried out in the form of a fractional sublimation.

| Ex. | Ligand L | Co-ligand CL | Ir complex Step 1: reaction temp./ reaction time/ suspension medium Step 2: extractant | Yield |
|---|---|---|---|---|
| 12 | 3 | 123-54-6 CL1 | | 16% |

Production and Characterisation of Organic Electroluminescent Devices Comprising the Compounds According to the Invention Electroluminescent devices according to the invention can be produced as described, for example, in WO 05/003253. The results for various OLEDs are compared here. The basic structure, the materials used, the degree of doping and the layer thicknesses thereof are identical for better comparability. OLEDs having an identical structure and comprising the dopants according to the invention are described. The following device structure is used here:

| Hole-injection layer (HIL) | 20 nm of 2,2',7,7'-tetrakis(di-para-tolyl-amino)spiro-9,9'-bifluorene |
| Hole-transport layer (HTL) | 5 nm of NPB (N-naphthyl-N-phenyl-4,4'-diaminobiphenyl) |
| Electron-blocking layer (EBL) | 15 nm of EBM (9,9-bis-(3,5-diphenyl-aminophenyl)fluorene) |
| Emission layer (EML) | 40 nm of host material M Dopant: 10% by vol. doping; compounds see Table 1. |
| Electron conductor (ETL) | 20 nm of BAlq |
| Cathode | 1 nm of LiF, 100 nm of Al on top. |

The structures of EBL and M are depicted below for clarity.

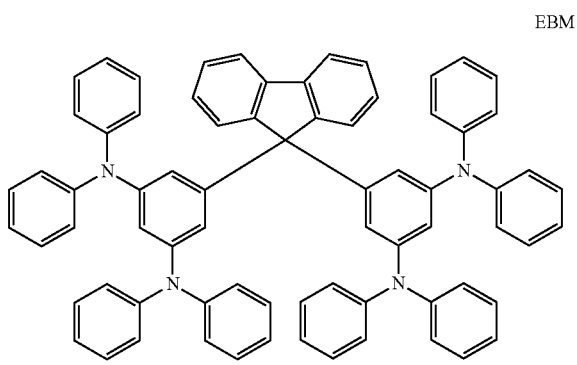

EBM

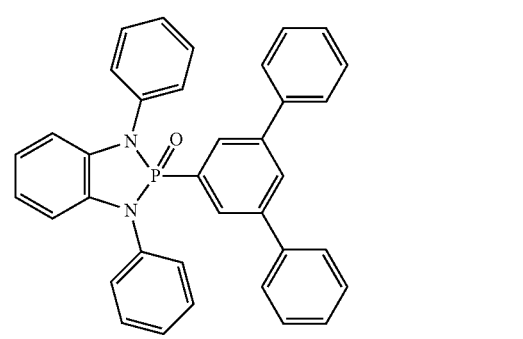

M

These as yet unoptimised OLEDs are characterised by standard methods; for this purpose, the electroluminescence spectra, the external quantum efficiency (measured in %) as a function of the luminance, calculated from current-voltage-luminance characteristic lines (IUL characteristic lines), are determined.

TABLE 1

Device results

| Ex. | Dopant | EQE at 100 cd/m$^2$ [%] | Voltage at 100 cd/m$^2$ [V] | CIE x/y |
|---|---|---|---|---|
| 13 | Ex. 1 | 11.3 | 5.8 | 0.19/0.45 |
| 14 | Ex. 2 | 12.0 | 5.6 | 0.18/0.39 |
| 15 | Ex. 4 | 9.9 | 3.7 | 0.40/0.56 |
| 16 | Ex. 6 | 6.8 | 6.9 | 0.16/0.25 |
| 17 | Ex. 7 | 2.3 | 5.0 | 0.67/0.32 |
| 18 | Ex. 8 | 10.4 | 4.8 | 0.40/0.55 |
| 19 | Ex. 9 | 9.8 | 4.3 | 0.39/0.55 |
| 20 | Ex. 10 | 11.2 | 4.6 | 0.40/0.54 |
| 21 | Ex. 11 | 12.0 | 4.5 | 0.52/0.45 |
| 22 | Ex. 12 | 10.8 | 5.0 | 0.42/0.54 |

The invention claimed is:
1. A compound of the formula (1)

formula (1)

where the compound of the general formula (1) contains a moiety $M(L)_n$ of the formula (2):

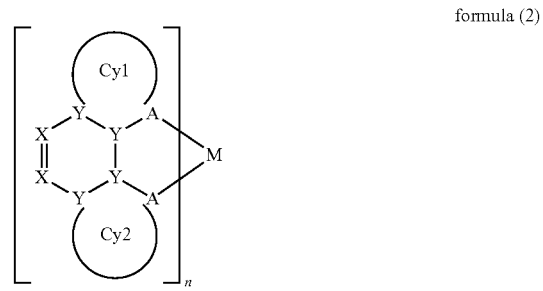

formula (2)

where the following applies to the symbols and indices used:

M is a metal;
Y is on each occurrence, identically or differently, C or N; a double bond may in each case also be present between the two atoms Y or between the adjacent atoms Y and A which are bonded in Cy1, or between the two atoms Y or the adjacent atoms Y and A which are bonded in Cy2;
Cy1 is selected from the structures of the following formulae (3) to (26):

formula (3)

formula (4)

formula (5)

-continued
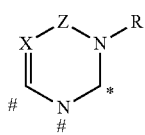
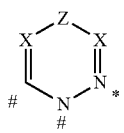
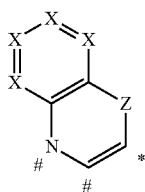
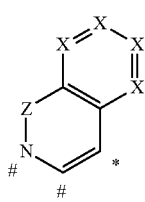
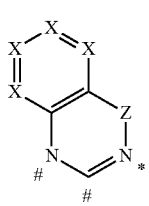
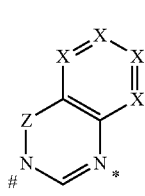
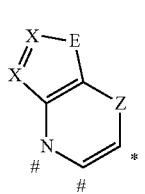
-continued
formula (6)
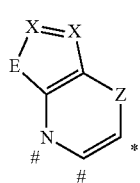
formula (7)
formula (8)
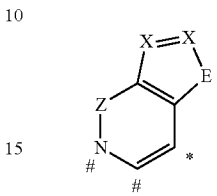
formula (9)
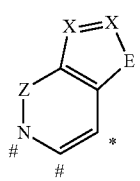
formula (10)
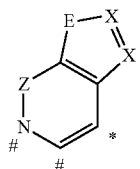
formula (11)
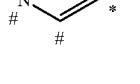
formula (12)
formula (13)
formula (14)
formula (15)
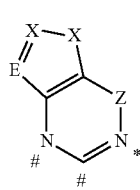
formula (16)
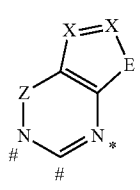
formula (17)
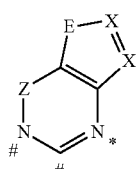
formula (18)
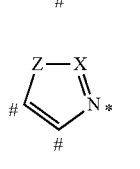
formula (19)
formula (20)
formula (21)
formula (22)
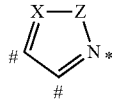
formula (23)

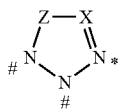

formula (24)

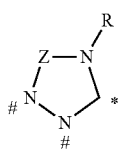

formula (25)

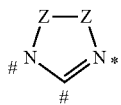

formula (26)

where E stands, identically or differently on each occurrence, for S, O or NR;
where * indicates the position of the coordination to the metal;
where # indicates the bond to Cy2 or to X in the ligand L;
Z is, identically or differently on each occurrence, C(=O), C(=S), CR$_2$, NR, O, S, PR or P(=O)R, where at least one group Z is equal to C(=O), C(=S), CR$_2$ or P(=O)R if Cy1 represents a five-membered ring;
Cy2 is on each occurrence, identically or differently, Cy1 or is on each occurrence, identically or differently, an aryl or heteroaryl group together with the group A and the two groups Y, where both groups Y in Cy2 stand for C if Cy2 stands for a six-membered aryl or heteroaryl ring group; Cy2 here optionally is substituted by one or more radicals R;
A is on each occurrence, identically or differently, C or N;
X is on each occurrence, identically or differently, CR or N;
R is on each occurrence, identically or differently, H, D, F, Cl, Br, I, N(R$^1$)$_2$, P(R$^1$)$_2$, CN, NO$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, OH, SH, O$^-$, S$^-$, N(R$^1$)$^-$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which optionally is substituted by one or more radicals R$^1$, where one or more non-adjacent CH$_2$ groups optionally is replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, O, S or CONR$^1$ and where one or more H atoms optionally is replaced by D, F, Cl, Br, I, CN or NO$_2$, or an aromatic or heteroaromatic ring system having 5 to 60 aromatic ring atoms, which in each case be optionally substituted by one or more radicals R$^1$, or an aryloxy or heteroaryloxy group having 5 to 60 aromatic ring atoms, which optionally is substituted by one or more radicals R$^1$, or a diarylamino group, diheteroarylamino group or arylheteroarylamino group having 10 to 40 aromatic ring atoms, which optionally is substituted by one or more radicals R$^1$; two or more adjacent radicals R here may also form a mono- or polycyclic, aliphatic, aromatic and/or benzo-fused ring system with one another;
R$^1$ is on each occurrence, identically or differently, H, D, F, Cl, Br, I, N(R$^2$)$_2$, CN, NO$_2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which optionally is substituted by one or more radicals R$^2$, where one or more non-adjacent CH$_2$ groups optionally is replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms optionally is replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which optionally is substituted by one or more radicals R$^2$, or a diarylamino group, diheteroarylamino group or arylheteroarylamino group having 10 to 40 aromatic ring atoms, which optionally is substituted by one or more radicals R$^2$; two or more adjacent radicals R$^1$ here may form a mono- or polycyclic, aliphatic or aromatic ring system with one another;
R$^2$ is on each occurrence, identically or differently, H, D, F or an aliphatic, aromatic and/or heteroaromatic organic radical having 1 to 20 C atoms, in which, in addition, one or more H atoms optionally is replaced by D or F; two or more substituents R$^2$ here may also form a mono- or polycyclic, aliphatic or aromatic ring system with one another;
L' is, identically or differently on each occurrence, any desired co-ligand;
anion is anion;
n is 1, 2 or 3;
m is 0, 1, 2, 3 or 4;
w is 1, 2 or 3;
x, y, z are on each occurrence, identically or differently, 0, 1, 2 or 3, where (w·x)=(y·z);
a plurality of ligands L here may also be linked to one another or L optionally is linked to L' via any desired bridge V and thus form a tridentate, tetradentate, pentadentate or hexadentate ligand system.

2. The compound according to claim 1, wherein the indices x=y=z=0, (the complexes are uncharged).

3. The compound according to claim 1, wherein M stands for a transition metal or for a main-group metal.

4. The compound according to claim 1, wherein M is selected from the group consisting of tin, chromium, molybdenum, tungsten, rhenium, ruthenium, osmium, rhodium, iridium, nickel, palladium, platinum, copper, silver and gold.

5. The compound according to claim 1, wherein one group A in the ligands L stands for a nitrogen atom and the other group A stands for a carbon atom.

6. The compound according to claim 1, wherein Cy1 contains precisely one group Z.

7. The compound according to claim 1, wherein Cy2 is selected from structures of the formulae (3) to (26) according to claim 1 or is selected from structures of the formulae (27) to (44):

formula (27)

formula (28)

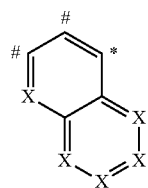

formula (29)

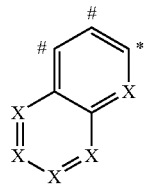

formula (30)

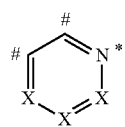

formula (31)

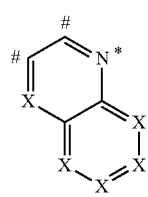

formula (32)

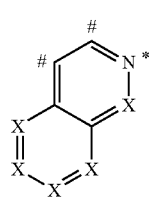

formula (33)

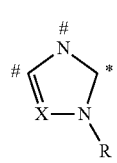

formula (34)

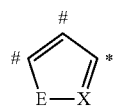

formula (35)

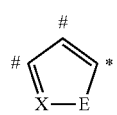

formula (36)

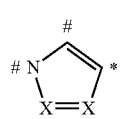

formula (37)

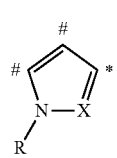

formula (38)

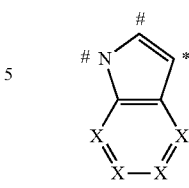

formula (39)

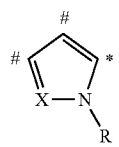

formula (40)

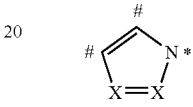

formula (41)

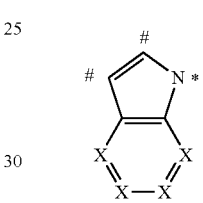

formula (42)

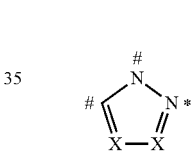

formula (43)

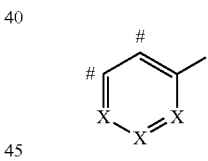

formula (44)

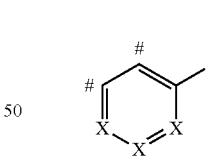

where the symbols used have the same meanings as described in claim 1.

8. The compound according to claim 1, wherein a maximum of three symbols X in each group stand for N.

9. The compound according to claim 1, wherein the group Z stands for C(=O) or CR$_2$.

10. The compound according to claim 1, wherein the group Z is C(=O).

11. The compound according to claim 1, wherein a bridging unit V is present which links L to one or more further ligands L or L', selected from structures of the formulae (51) to (55):

formula (51)
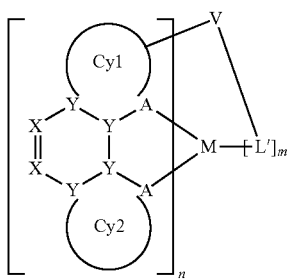

formula (52)
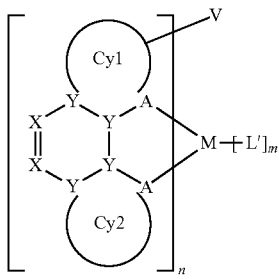

formula (53)
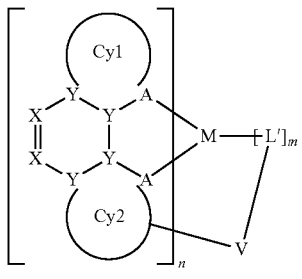

formula (54)
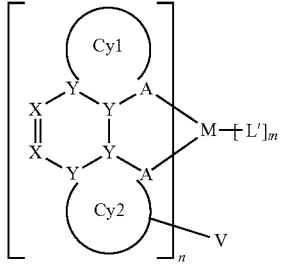

formula (55)
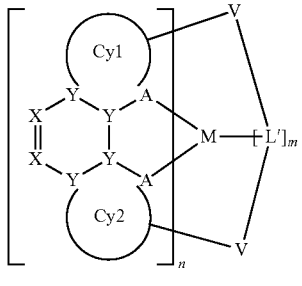

where the symbols used have the meanings given in claim 1, and V represents a bridging unit containing 1 to 80 atoms from the third, fourth, fifth, and/or sixth main group or a 3- to 6-membered homo- or heterocycle which covalently bonds the part-ligands L to one another or covalently bonds L to L'; V here may also be substituted by one or more radicals $R^1$.

12. The compound according to claim 1, wherein the ligands L' are carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, $F^-$, $Cl^-$, $Br^-$, $I^-$, alkylacetylides, arylacetylides, cyanide, cyanate, isocyanate, thiocyanate, isothiocyanate, aliphatic or aromatic alcoholates, aliphatic or aromatic thioalcoholates, amides, carboxylates, aryl groups, $O^{2-}$, $S^{2-}$, carbides, nitrenes, $N^{3-}$, diamines, imines, diimines, heterocycles containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, dithiolates derived from dithiols, borates of nitrogen-containing heterocycles, or bidentate ligands which consist of a combination of two groups of the formulae (70) to (97), where one group is bonded via a neutral nitrogen atom or a carbene atom and the other group is bonded via a negatively charged carbon atom or a negatively charged nitrogen atom:

formula (70)
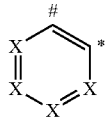

formula (71)
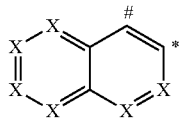

formula (72)
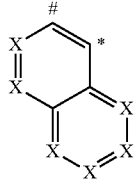

formula (73)
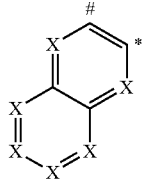

formula (74)
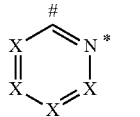

formula (75)
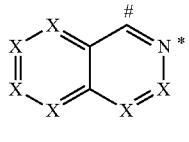

formula (76)
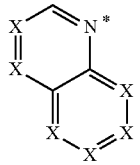

-continued
formula (77)
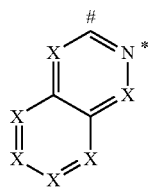
formula (78)
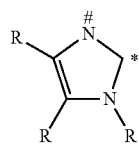
formula (79)
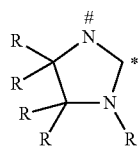
formula (80)
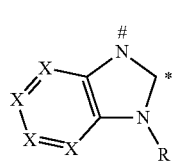
formula (81)
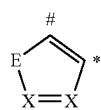
formula (82)
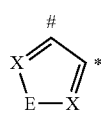
formula (83)
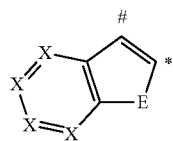
formula (84)
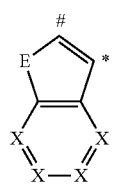
formula (85)
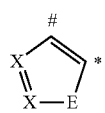
formula (86)
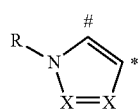
-continued
formula (87)
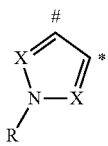
formula (88)
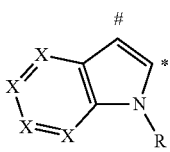
formula (89)
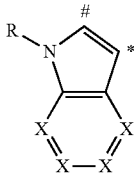
formula (90)
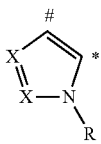
formula (91)
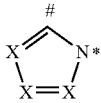
formula (92)
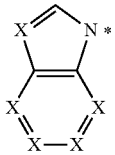
formula (93)
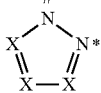
formula (94)
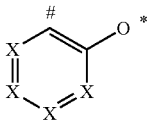
formula (95)
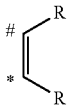
formula (96)
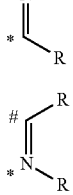
formula (97)

where the symbols used have the same meanings as described in claim 1;

or η⁵-cyclopentadienyl, η⁵-pentamethylcyclopentadienyl, η⁶-benzene or η⁷-cycloheptatrienyl, each of which optionally is substituted by one or more radicals R¹, or 1,3,5-cis-cyclohexane derivatives, 1,1,1-tri(methylene) methane derivatives or 1,1,1-trisubstituted methanes.

13. A process for the preparation of the compound according to claim 1, which comprises reacting the free ligands L and optionally L' with metal alkoxides of the formula (102), with metal ketoketonates of the formula (103), with metal halides of the formula (104) or with dimeric metal complexes of the formula (105):

M(OR¹)ₙ    formula (102)

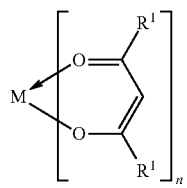    formula (103)

MHalₙ    formula (104)

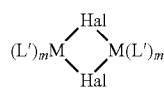    formula (105)

where the symbols and indices M, L', m, n and R¹ have the meanings indicated in claim 1, and Hal=F, Cl, Br or I.

14. An electronic device comprising at least one compound according to claim 1.

15. The electronic device as claimed in claim 13, wherein the electronic device is selected from the group consisting of organic electroluminescent device (OLED, PLED), organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD), light-emitting electrochemical cell (LEC) or organic laser diode (O-laser).

16. An organic electroluminescent device which comprises the compound according to claim 1, is employed as emitting compound in one or more emitting layers.

17. An organic electroluminescent device which comprises the compound according to claim 1, is employed as emitting compound in one or more emitting layers, in combination with a matrix material wherein the matrix material is selected from the group consisting of ketones, phosphine oxides, sulfoxides, sulfones, triarylamines, carbazole derivatives, indolocarbazole derivatives, indenocarbazole derivatives, azacarbazoles, bridged carbazole derivatives, bipolar matrix materials, silanes, azaboroles, boronic esters, triazine derivatives, zinc complexes, diaza- or tetraazasilole derivatives, diazaphosphole derivatives, and mixtures thereof.

18. A compound of the formula (1)

[M(L)ₙ(L')ₘ]w^{x+}(anion)_y^{z−}    formula (1)

where the compound of the general formula (1) contains a moiety M(L)ₙ of the formula (45):

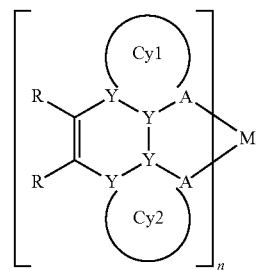    formula (45)

wherein

Cy1 is selected from the structures of the following formulae (3) to (26):

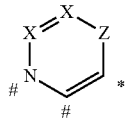    formula (3)

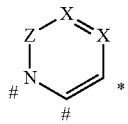    formula (4)

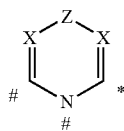    formula (5)

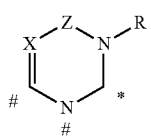    formula (6)

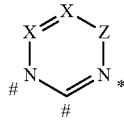    formula (7)

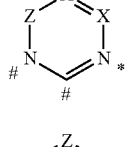    formula (8)

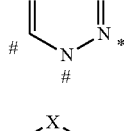    formula (9)

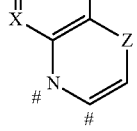    formula (10)

formula (11)

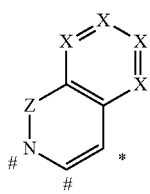

formula (12)

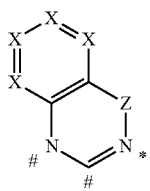

formula (13)

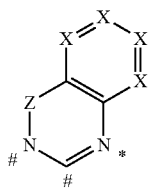

formula (14)

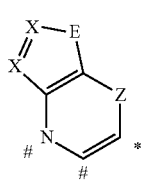

formula (15)

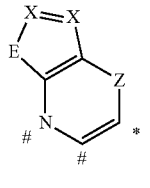

formula (16)

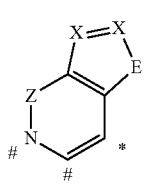

formula (17)

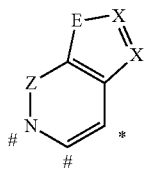

formula (18)

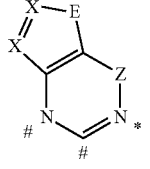

formula (19)

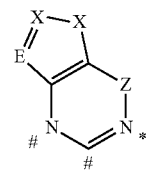

formula (20)

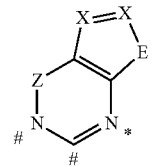

formula (21)

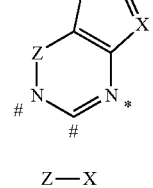

formula (22)

formula (23)

formula (24)

formula (25)

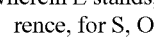

formula (26)

wherein E stands, identically or differently on each occurrence, for S, O or NR, \* indicates the position of the coordination to the metal, and where # indicates the bond to Cy2 or to X in the ligand L, Cy2 is selected from structures of the formulae (3) to (26) above or is selected from structures of the formulae (27) to (44):

formula (27)

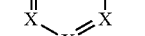

-continued

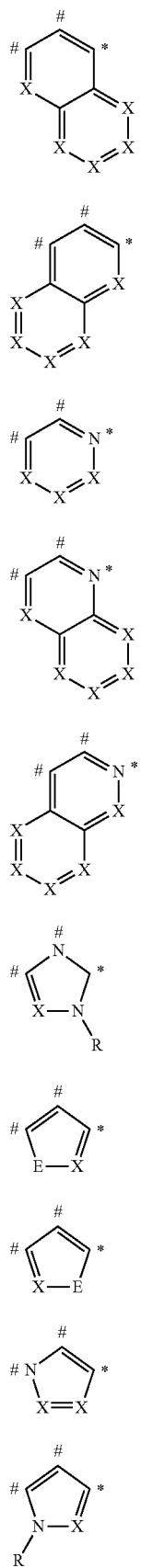

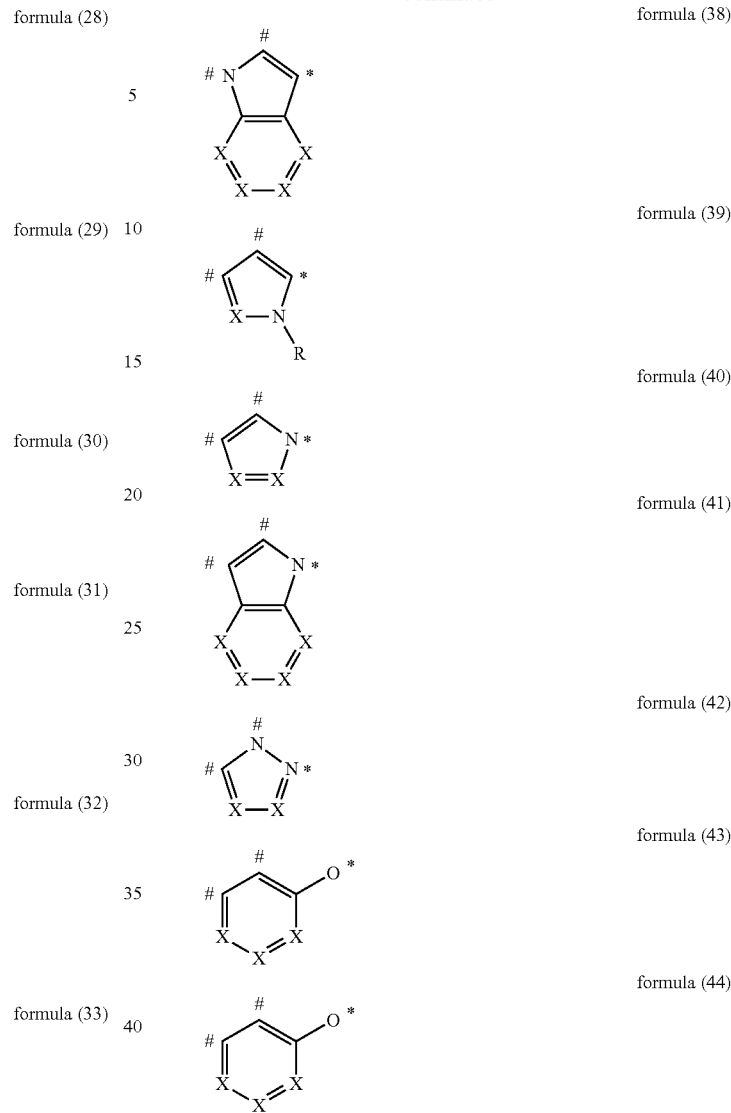

M is selected from the group consisting of tin, chromium, molybdenum, tungsten, rhenium, ruthenium, osmium, rhodium, iridium, nickel, palladium, platinum, copper, silver and gold;

Y is on each occurrence, identically or differently, C or N; a double bond may in each case also be present between the two atoms Y or between the adjacent atoms Y and A which are bonded in Cy1, or between the two atoms Y or the adjacent atoms Y and A which are bonded in Cy2;

Z is, identically or differently on each occurrence, C(=O), C(=S), $CR_2$, NR, O, S, PR or P(=O)R, where at least one group Z is equal to C(=O), C(=S), $CR_2$ or P(=O)R if Cy1 represents a five-membered ring;

A is on each occurrence, identically or differently, C or N;

X is on each occurrence, identically or differently, CR or N and wherein a maximum of one symbol X for each group stands for N;

R is on each occurrence, identically or differently, H, D, F, Cl, Br, I, $N(R^1)_2$, $P(R^1)_2$, CN, $NO_2$, $Si(R^1)_3$, $B(OR^1)_2$, $C(=O)R^1$, $P(=O)(R^1)_2$, $S(=O)R^1$, $S(=O)_2R^1$, $OSO_2R^1$, OH, SH, $O^-$, $S^-$, $N(R^1)^-$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which optionally is substituted by one or more radicals $R^1$, where one or more non-adjacent $CH_2$ groups optionally is replaced by $R^1C=CR^1$, $C≡C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms optionally is replaced by D, F, Cl, Br, I, CN or $NO_2$, or an aromatic or heteroaromatic ring system having 5 to 60 aromatic ring atoms, which in each case be optionally substituted by one or more radicals $R^1$, or an aryloxy or heteroaryloxy group having 5 to 60 aromatic ring atoms, which optionally is substituted by one or more radicals $R^1$, or a diarylamino group, diheteroarylamino group or arylheteroarylamino group having 10 to 40 aromatic ring atoms, which optionally is substituted by one or more radicals $R^1$; two or more adjacent radicals R here may also form a mono- or polycyclic, aliphatic, aromatic and/or benzo-fused ring system with one another;

$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which optionally is substituted by one or more radicals $R^2$, where one or more non-adjacent $CH_2$ groups optionally is replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms optionally is replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which optionally is substituted by one or more radicals $R^2$, or a diarylamino group, diheteroarylamino group or arylheteroarylamino group having 10 to 40 aromatic ring atoms, which optionally is substituted by one or more radicals $R^2$; two or more adjacent radicals $R^1$ here may form a mono- or polycyclic, aliphatic or aromatic ring system with one another;

$R^2$ is on each occurrence, identically or differently, H, D, F or an aliphatic, aromatic and/or heteroaromatic organic radical having 1 to 20 C atoms, in which, in addition, one or more H atoms optionally is replaced by D or F; two or more substituents $R^2$ here may also form a mono- or polycyclic, aliphatic or aromatic ring system with one another;

L' is, identically or differently on each occurrence, any desired co-ligand;

anion is anion;

n is 1, 2 or 3;

m is 0, 1, 2, 3 or 4;

w is 1, 2 or 3;

x, y, z are on each occurrence, identically or differently, 0, 1, 2 or 3, where $(w·x)=(y·z)$;

a plurality of ligands L here may also be linked to one another or L optionally is linked to L' via any desired bridge V and thus form a tridentate, tetradentate, pentadentate or hexadentate ligand system.

\* \* \* \* \*